(12) United States Patent
Gibson et al.

(10) Patent No.: US 8,435,736 B2
(45) Date of Patent: *May 7, 2013

(54) METHOD FOR IN VITRO RECOMBINATION

(75) Inventors: Daniel Glenn Gibson, Crofton, MD (US); Hamilton O. Smith, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 111 days.

This patent is subject to a terminal disclaimer.

(21) Appl. No.: 12/820,861

(22) Filed: Jun. 22, 2010

(65) Prior Publication Data

US 2010/0311126 A1   Dec. 9, 2010

Related U.S. Application Data

(63) Continuation of application No. 11/502,624, filed on Aug. 11, 2006, now Pat. No. 7,776,532.

(60) Provisional application No. 60/707,177, filed on Aug. 11, 2005, provisional application No. 60/800,400, filed on May 16, 2006.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.2; 536/23.1; 536/24.3

(58) Field of Classification Search .................. None
See application file for complete search history.

(56) References Cited

U.S. PATENT DOCUMENTS

| 4,582,802 A | * | 4/1986 | Zimmerman et al. | ....... 435/91.4 |
| 6,379,964 B1 | | 4/2002 | del Cardayre et al. | |
| 6,521,427 B1 | * | 2/2003 | Evans | .......... 435/91.1 |
| 2007/0037197 A1 | * | 2/2007 | Young et al. | ...... 435/6 |

FOREIGN PATENT DOCUMENTS

WO   WO 98/38297   *   9/1998

OTHER PUBLICATIONS

Tabor, S, Curr. Prot. Mol. Biol., 3.11.1-3.11.4 (2000).*
New England biolabs Catalog, p. 69 (1993/94).*
Kaslin, E. et al., J. Biol. Chem., vol. 269, pp. 14094-14102 (1994).*
Zimmerman, S. et al., Nucl. Acids res., vol. 13, pp. 2241-2249 (1985).*
Zimmerman, S. et al., PNAS USA, vol. 84, pp. 1871-1875 (1987).*
Lai and Masker, "Repair of double-strand breaks by incorporation of a molecule of homologous DNA", *Mol. Microbiol.*, 36(2):437-46 (2000).

* cited by examiner

*Primary Examiner* — Teresa E Strzelecka
(74) *Attorney, Agent, or Firm* — DLA Piper LLP (US)

(57) ABSTRACT

The present invention relates to an in vitro method, using isolated protein reagents, for joining two double-stranded (ds) DNA molecules of interest, wherein the distal region of the first DNA molecule and the proximal region of the second DNA molecule share a region of sequence identity. The method allows the joining of a number of DNA fragments, in a predetermined order and orientation, without the use of restriction enzymes. It can be used, e.g., to join synthetically produced sub-fragments of a gene or genome of interest.

26 Claims, 5 Drawing Sheets

METHOD FOR IN VITRO RECOMBINATION

CROSS-REFERENCE TO RELATED APPLICATION

This application is a continuation of U.S. Ser. No. 11/502,624 filed Aug. 11, 2006 which claims priority of U.S. Provisional Patent Application Ser. No. 60/707,177, filed Aug. 11, 2005, and of U.S. Provisional Patent Application Ser. No. 60/800,400, filed May 16, 2006. The contents of these applications are herein incorporated by reference in their entireties.

STATEMENT OF RIGHTS TO INVENTIONS MADE UNDER FEDERALLY SPONSORED RESEARCH

This invention was made with government support under Grant No. DE-FG02-02ER63453 awarded by the Department of Energy. The government has certain rights in the invention.

FIELD OF THE INVENTION

This invention relates, e.g., to in vitro methods, using isolated proteins, for joining (recombining) double-stranded, overlapping DNA molecules.

DESCRIPTION OF THE INVENTION

Figure 1:
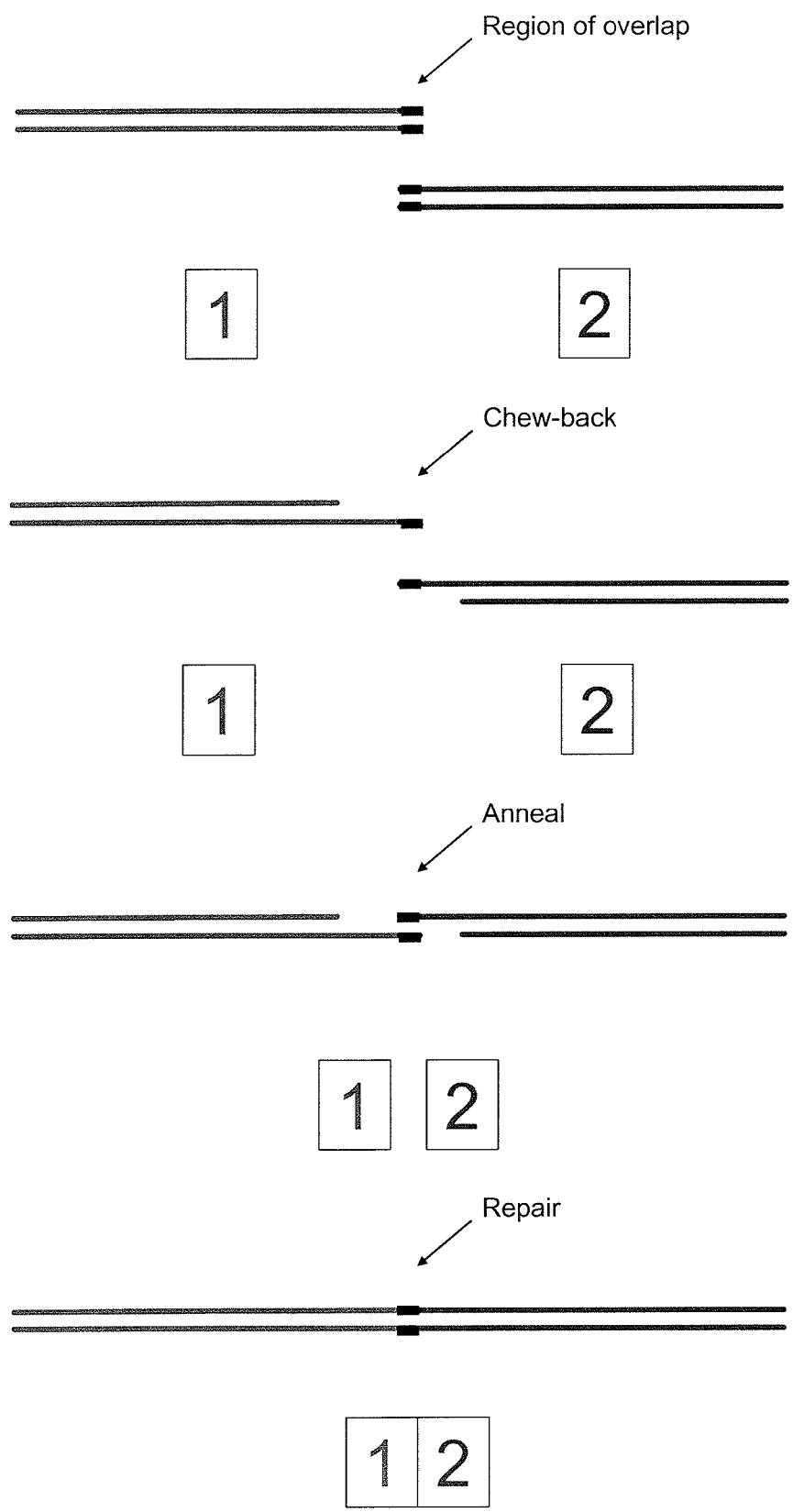
FIG. 1 illustrates schematically a method for joining (recombining) two DNAs with overlapping homology at their ends (denoted with a thickened line), using a 3'-5' exonuclease.

The present inventors have identified combinations of isolated proteins (e.g., enzymes) and suitable reaction conditions for the efficient in vitro joining of two or more double-stranded DNA molecules which share overlapping regions of sequence homology (e.g., sequence identity) at their ends.

In brief, the method comprises (1) a "chew-back" step, in which an exonuclease chews back ends of the double-stranded DNA molecules, to expose single-stranded overhangs comprising the regions of overlap; (2) an annealing step, in which the single-stranded overhangs are annealed (hybridized) specifically; and (3) a repair step, in which remaining single-stranded gaps in the annealed molecules are filled in and nicks thus formed are sealed (ligated). The region of sequence homology generally comprises at least about 20 non-palindromic nucleotides (nt), e.g., at least about 40 non-palindromic nt. A "single-stranded gap," as used herein, refers to a single-stranded region of a nucleic acid wherein the surrounding regions are double-stranded. The method allows, e.g., for the joining of DNA molecules of interest to one another in a predefined order and orientation, without the use of (or with very limited use of) restriction enzymes.

In one embodiment of this method, an enzyme having a 3'→5' exonuclease activity generates 5' single-stranded overhangs in each of two DNA molecules to be joined, wherein the single-stranded overhangs comprise the region of sequence homology (e.g., identity). The two single-stranded overhangs anneal to form a gapped molecule; a DNA polymerase fills in the gaps; and a ligase seals the nicks. This embodiment of the method is illustrated schematically in FIG. 1. In another embodiment of the method, the enzyme in the first step has a 5'→3' exonuclease activity, and 3' single-stranded overhangs are generated and then joined. A variety of different enzymes can be used in the different steps of the method.

The "joining" of two DNA molecules is sometimes referred to herein as "recombination" of the two DNA molecules. In the method of the invention, the proteins having exonuclease, polymerase and ligase activities are isolated (e.g., substantially purified); cell extracts or intact cells are not employed.

The method can be used to join more than two DNA molecules. To accomplish this, the DNA molecules to be joined are designed such that, for each pair of DNA molecules to be joined, the distal region of one DNA molecule comprises a region of sequence homology (e.g., identity) with the proximal region of the other DNA molecule. To facilitate the joining of the DNA molecules in a predetermined orientation and order, each set of distal and proximal regions of sequence identity is selected (designed) to be unique (to be different from the regions of sequence identity of the other pairs of DNA molecules). The method allows a number of DNA molecules to be joined (e.g., in a single reaction mixture, and a single tube).

In one embodiment, the DNA molecules which are joined are synthetically generated DNA molecules which lie adjacent to one another in a gene or genome of interest. For example, a first set of about 4-8 such DNA molecules of about 5-6 kilobase pairs (kb) each are joined in the proper order and orientation according to a method of the invention. A second set of a similar number of adjoining DNA molecules of about the same size are also joined; and then, in a second stage assembly, the two sets of joined molecules are joined to one another. The process is repeated with further sets of DNA molecules, in as many cycles as desired. In such a manner, the component elements of a gene or genome, all or nearly all of which have been generated synthetically, can be joined in sequential steps to form a complete gene or genome.

A method of the invention can be used to join any DNA molecules of interest, including DNAs which are naturally occurring, cloned DNA molecules, synthetically generated DNAs, etc. The joined DNA molecules may, if desired, be cloned into a vector (e.g., using a method of the invention).

Advantages of the method of the invention include the ability to perform the joining (recombination) reactions under well-defined conditions, using well-characterized, isolated (e.g., substantially purified) proteins (e.g., enzymes). This allows the joining reactions to be controlled and reproducible. In a method of the invention, the joining process is not subject to competing reactions brought about by other enzymes in the reaction mixture, such as exonucleases and endonucleases which can be present in cells or cell extracts. The method of the invention requires very little sample handling and can be completed rapidly (e.g., within 1-2 hours). In some embodiments, the joining of a desired set of nucleic acid molecules is performed in a single vessel, such as a tube in a thermocycler apparatus. If a thermocycler is used, a researcher only needs to be present, e.g., to initiate the chew-back reaction and to add the repair mix after the annealing process is complete. If desired, the steps of the method can be carried out robotically, without the intervention of an investigator, allowing for high throughput joining (assembly) to occur.

The ability to join DNA molecules in a defined order and orientation allows, for example, for the cloning of one or more fragments of interest into a linearized vector in a defined orientation; or for the assembly of component DNA portions of a longer sequence of interest (such as the assembly of component parts of a synthetic gene or genome); or for the assembly and cloning of sub-fragments of a DNA which are too large to clone using a PCR amplification step. The method allows one to join and/or clone DNA molecules of interest without having to rely on the presence of restriction enzyme recognition sites at the ends of the fragments to be joined. The in vitro procedure also allows one to assemble DNAs that are unstable or otherwise recalcitrant to in vivo cloning, and thus would be difficult to clone by a method requiring transformation into and replication in a bacterium. If desired, DNAs assembled by a method of the invention can then be amplified in vitro (e.g., by multiple displacement amplification (MDA), such as rolling circle amplification (RCA); or by PCR), again without having to passage the DNA through a bacterium.

One aspect of the invention is an in vitro method, using isolated (e.g., substantially purified) proteins, for joining two or more double-stranded (ds) DNA molecules of interest, wherein the distal region of the first DNA molecule and the proximal region of the second DNA molecule of each pair share a region of sequence identity, comprising
 (a) treating the DNA molecules with an enzyme having an exonuclease activity, under conditions effective to yield single-stranded overhanging portions of each DNA molecule which contain a sufficient length of the region of sequence homology to hybridize specifically to the region of sequence homology of its pair;
 (b) incubating the treated DNA molecules of (a) under conditions effective to achieve specific annealing of the single-stranded overhanging portions; and
 (c) treating the incubated DNA molecules in (b) under conditions effective to fill in remaining single-stranded gaps and to seal the nicks thus formed.

In one aspect of the invention, the region of sequence identity comprises at least about 20, 30 or 40 non-palindromic nucleotides (nt), e.g., at least about 80, 300 or 500 nt.

In one aspect of the method, a crowding agent (such as PEG, e.g., at a concentration of about 5%) is present in the reaction mixture at each of steps (a), (b) or (c); and/or, in (c) the DNA molecules are treated with Taq DNA polymerase and a compatible ligase, such as Taq ligase.

In (a), the enzyme may have a 3'→5' exonuclease activity (e.g., an exonuclease, such as exonuclease III; or a DNA polymerase, such as T4 DNA polymerase, T7 DNA polymerase, DNA polymerase I, Klenow DNA polymerase, Phi 29 DNA polymerase, Pfu polymerase, Phusion™ High-Fidelity polymerase, Vent$_R$, Deep Vent$_R$, or 9°N$_m$ DNA polymerase, which exhibits exonuclease activity when it is incubated under suitable conditions, such as the absence of added dNTPs).

In (b), the treated molecules of (a) may be incubated (e.g., at about 75° C.) under conditions effective to separate the strands of the overhangs which have annealed and, optionally, to inactivate the enzyme, and then slowly cooled to about 24° C. (e.g., about 23° C.) or less, under conditions effective to allow the single-stranded overlaps to anneal. Alternatively, specific annealing of the single-stranded overhanging portions may be achieved by including in the treating step in (a) a protein that enhances the binding of the single-stranded overhanging portions, e.g., E. coli RecA, E. coli single-stranded binding protein (SSB), T7 SSB (T7 gene 2.5 product), or T4 gene 32 protein.

In (c), the conditions effective to fill in remaining single-stranded gaps and to seal the nicks may comprise incubating the annealed DNA molecules with a DNA polymerase in the presence of dNTPs and a compatible ligase. In one embodiment, the DNA polymerase is T4, T7, E. coli PolI, Klenow, Taq, Phusion™ or Pfu polymerase; the ligase is T4, E. coli or Taq DNA ligase or Ampligase®; and the treatment is performed at about 37° C. In another embodiment, the DNA polymerase is Taq, Phusion™ or Pfu DNA polymerase; the ligase is Taq DNA ligase or Ampligase®; and the treatment is performed at about 45° C.

One aspect of the invention is an in vitro method, using isolated (e.g., substantially purified) proteins, for joining at least two ds DNA molecules of interest, each of about 5-6 kilobases (kb), wherein the distal region of the first DNA molecule and the proximal region of the second DNA molecule of each pair share a unique region of sequence identity, comprising
 (a) treating approximately equimolar amounts of the DNA molecules with T4 DNA polymerase at about 37° C., in a solution comprising about 0.2 M Tris at about pH 7.5, in the absence of added dNTPs, under conditions effective to chew-back at least the regions of sequence identity in each molecule, thereby forming single-stranded overhanging ends of sufficient length to hybridize specifically to overhangs having the complement of the shared region of sequence identity;
 (b) annealing the treated DNA molecules in (a) by incubating them at about 75° C. for about 20 minutes, and slow cooling them to about 24° C. or less, under conditions effective to anneal the single-stranded DNA regions which were generated during (a); and
 (c) incubating the cooled DNA molecules in (b) with Taq DNA polymerase and Taq DNA ligase at about 45° C., in the presence of added dNTPs, under conditions effective to fill in the gaps and seal the nicks,
 wherein about 5% PEG is present throughout the joining procedure.

Another aspect of the invention is an in vitro method, using isolated (e.g., substantially purified) proteins, for joining at least two dsDNA molecules of interest, each of about 5-6 kilobases (kb), wherein the distal region of the first DNA molecule and the proximal region of the second DNA molecule of each pair share a unique region of sequence identity, comprising
 (a) incubating approximately equimolar amounts of the DNA molecules with: T4 DNA polymerase; a protein that enhances annealing of single-stranded DNAs (e.g., RecA, E. coli or T7 SSB, or T4 gene 32 product); and a ligase that is compatible with the polymerase, at about 37° C., in the absence of added dNTPs, under conditions effective to chew-back at least the regions of sequence identity in each molecule, thereby forming single-stranded overhanging ends of sufficient length to hybridize specifically to overhangs having the complement of the shared region of sequence identity, and to allow hybridization of the single-stranded overhangs, thereby forming gapped molecules; and (b) incubating the gapped DNA molecules of (a) with a sufficient amount of dNTPs, under conditions effective to allow filling in of the gaps, generation of nicks, and sealing of the nicks, wherein the method is carried out in a single vessel.

Another aspect of the invention is an isothermal method similar to the preceding method, except the ligase is not present during the initial chew-back/annealing reaction, but instead is added with the dNTPs during the repair reaction.

The methods of the invention may be used to join at least about 4 (e.g., at least about 6 or 8) double-stranded DNA molecules, wherein for each pair of molecules to be joined, the distal region of one DNA molecule comprises a region of sequence homology to the proximal region of the other DNA molecule, and each set of distal and proximal regions of homology is unique for each pair of DNA molecules to be joined.

In methods of the invention, the DNA molecules to be joined can be at least about 5 kb (e.g., at least about 25 kb, 140 kb, 500 kb, or $1 \times 10^6$ bp).

Methods of the invention can be carried out in a single vessel (tube, vial, etc.). For example, in one embodiment, the chew-back and annealing steps are carried out in a solution that comprises about 0.2M Tris-Cl, pH 7.5 and about 5% PEG; and when the chew-back/annealing reactions are complete, the reaction mixture is diluted 1:4; more PEG is added to a final concentration of about 5%; and the repair reaction is allowed to proceed.

The DNA molecules of interest can comprise a vector DNA molecule, and the joined DNAs of interest can thus be cloned into the vector.

In methods of the invention, one or more (e.g., all) of the plurality of DNA molecules are generated synthetically, or are copies of DNA that has been generated synthetically. The DNA molecules may be adjacent sequences of a gene or genome of interest. In one embodiment, the DNA molecules are synthesized so as to comprise overlapping regions of sequence identity at their ends, and the DNA molecules are joined to form part or all of a synthetic gene or genome.

A method of the invention can further comprise repeating the method to join a second set of two or more DNA molecules of interest to one another, and then repeating the method again to join the first and second set DNA molecules of interest.

Another aspect of the invention is a kit for implementing a method of the invention. The kit can comprise, e.g., (a) an isolated (e.g., substantially purified) enzyme having a 3' or 5' exonuclease activity (e.g., T4 DNA polymerase); (b) an isolated (e.g., substantially purified) non strand-displacing DNA polymerase (e.g., Taq DNA polymerase); (c) an isolated (e.g., substantially purified) ligase which is compatible with the non strand-displacing polymerase (e.g., when this DNA polymerase is Taq DNA polymerase, the ligase can be Taq DNA ligase); and, optionally, (d) a solution, or compounds for making a solution, which, when combined with the exonuclease and the dsDNA molecules to be joined, comprises about 5% PEG and/or about 0.2M Tris, at about pH 7.5. In another embodiment, the kit can comprise, e.g., (a) a vessel containing isolated (e.g., substantially purified) T4 DNA polymerase; a protein that enhances annealing of single-stranded DNAs; and a ligase that is compatible with the polymerase; and, optionally (b) a solution, or compounds for making a solution, which, when combined with an aliquot of the protein mixture in (a) and a plurality of suitable DNA molecules containing regions of sequence identity at their termini, is effective to allow chew-back of regions of sequence identity of the DNA molecules, the formation of single-stranded overhangs containing the regions of sequence identity, and hybridization of the single-stranded overhangs, thereby forming gapped molecules; and, optionally (c) a concentrated solution of dNTPs, or reagents for preparing such a solution, that, when added in a suitable volume to the solution in (b) which contains gapped molecules, and incubated with that solution under suitable conditions, is effective to allow filling in of the gaps. Each of the components of a kit of the invention can be in separate containers, or two or more components can be in the same container.

Another aspect of the invention is a composition comprising: (a) a purified (e.g., substantially purified) enzyme which, under suitable reaction conditions exhibits a 3' or 5' exonuclease activity (e.g., T4 DNA polymerase, wherein the suitable reaction conditions include the absence of added dNTPs); (b) a non strand-displacing DNA polymerase (e.g., Taq DNA polymerase); and (c) a DNA ligase which is compatible with the DNA polymerase in (b) (e.g., Taq DNA ligase); and, optionally, (d) about 0.2 M Tris, pH about 7.5 and/or about 5% PEG.

Another aspect of the invention is an in vitro method for joining two or more double stranded DNA molecules of interest, as discussed above, further wherein each of the DNA molecules of interest comprises, at the free end of the region of sequence identity, a restriction enzyme cleavage site (such as a Not I site) that is not present elsewhere in the DNA molecules of interest; the DNA molecules of interest are cleaved with the restriction enzyme; and during the repair steps, the restriction enzyme cleavage site is removed from the joined molecules.

Another aspect of the invention is an in vitro method, using isolated (e.g., substantially purified) proteins, for joining two or more single-stranded (ss) DNA molecules of interest, wherein the distal region of the first DNA molecule and the proximal region of the second DNA molecule of each pair share a region of sequence identity, comprising (a) incubating the single-stranded DNA molecules under conditions effective to achieve specific annealing of the regions of sequence identity, thereby forming molecules with single stranded gaps; and (b) treating the gapped molecules in (a) under conditions effective to fill in the gaps and to seal the nicks thus formed, wherein the region of sequence identity comprises at least 20 (e.g., at least about 40) non-palindromic nucleotides (nt) and, optionally, wherein a crowding agent (such as PEG, e.g., 5% PEG) is present during steps (a) and (b); and/or the molecules in step (b) are treated with Taq ligase; and/or a protein that enhances annealing of single-stranded DNAs (such as, e.g., RecA, a single-stranded binding protein, or T4 gene 32 protein) is present during steps (a) and (b).

Any of a variety of 3'→5' or 5'→3' or double-strand specific exodeoxyribonucleases may be used to chew-back the ends of DNA molecules in the methods of the invention. The term "3' exonuclease" is sometimes used herein to refer to a 3'→5' exodeoxyribonuclease. Digestion with a 3' exonuclease produces 5' single-stranded overhangs in the DNA molecules. The term "5' exonuclease" is sometimes used herein to refer to a 5'→3' exodeoxyribonuclease. Digestion with a 5' exonuclease produces 3' single-stranded overhangs in the DNA molecules. Methods for preparing and using exonucleases and other enzymes employed in methods of the invention are conventional; and many are available from commercial sources, such as USB Corporation, 26111 Miles Road, Cleveland, Ohio 44128, or New England Biolabs, Inc. (NEB), 240 County Road, Ipswich, Mass. 01938-2723.

One aspect of the invention is an in vitro joining method as above, wherein the enzyme in the first step exhibits a 5'→3' exonuclease activity. Examples of enzymes having a suitable 5' exonuclease activity include, e.g., phage T7 exonuclease (phage T7 gene 6 product), phage lambda exonuclease, Redα of lambda phage, or RecE of Rac prophage.

When a 5' exonuclease is used, single-stranded overhangs are generated at the 5' end of DNA molecules which cannot be repaired, unless, e.g., the molecules can form a circle, or other procedures are introduced to block exonuclease digestion of these 5' termini. Non-strand displacing DNA polymerases used in methods of the invention must elongate in the 5' direction from a primer molecule. Because no primer is available to be extended in the 5'-located gap in a DNA molecule which has been chewed back with a 5' exonuclease, the gap cannot be filled in by a polymerase. In one embodiment of the invention, the 5' ends of the terminal DNA fragments that are to be joined are blocked so that 5' exonuclease cannot digest them. The blocking agent is preferably reversible, so that the joined DNA molecule can eventually be joined into a vector. Suitable blocking agents will be evident to the skilled worker. These include, e.g., phosphorothioate bonds, 5' spacer molecules, locked nucleic acid (LNA), etc. In another embodiment of the invention, the fragments are selected (designed) so that the two terminal fragments join to one another to form a circle. In another embodiment, the joined fragments are designed so that they become integrated into a vector which is also present in the reaction mixture.

In one embodiment of the invention, the enzyme in the first step exhibits a 3'→5' exonuclease activity (sometimes referred to herein as a 3' exonuclease activity). Any of a variety of enzymes can be used in this step. For example, the enzyme can be a 3' exonuclease, such as exonuclease III. In another embodiment, the enzyme is a DNA polymerase which, when incubated under effective conditions, expresses a net 3' exonuclease activity. Suitable conditions include incubation in the absence of added dNTPs. (There may be a small amount of residual dNTPs in a reaction mixture, but these are not in a sufficient amount to allow the polymerase activity of the enzyme to cancel out the exonuclease activity.) Among the suitable DNA polymerases that can be used (in the absence of added dNTPs) are, e.g., T4 DNA polymerase, T7 DNA polymerase, E. coli DNA polymerase I, Klenow DNA polymerase, Phi 29 DNA polymerase, Pfu polymerase, Phusion™ High-Fidelity polymerase, Vent$_R$, Deep Vent$_R$, or 9° N$_m$ DNA polymerase. Preferably, the enzyme is T4 DNA polymerase or T7 DNA polymerase, which have very similar properties with respect to 3' exonuclease activity.

Advantages of T4 DNA polymerase include: (a) it provides excellent synchronicity in exposing single-stranded DNA; (b) the reactions can be easily controlled to expose different amounts of single-stranded DNA; (c) the exonuclease activity of T4 DNA polymerase does not degrade DNA as rapidly as other exonucleases and therefore, does not require large amounts of input DNA; and (d), like all the mesophilic DNA polymerases discussed herein, it can be heat-inactivated.

Under suitable conditions, which will be evident to the skilled worker, T4 DNA polymerase can chew-back DNA molecules having blunt ends, or 5' or 3' single-stranded overhangs.

Thermophilic polymerases (e.g., Vent) have the advantage that, because they operate at high temperatures, secondary structures in the DNA template may be removed at the high temperature, so the polymerase molecules are not slowed down by secondary structure. This permits more rapid exonuclease digestion than is accomplished with enzymes which function at lower temperatures, and allows for the digestion of longer overhangs. However, because of the stability of these enzymes at high temperatures, it is difficult to inactivate them by heat, and a more cumbersome procedure, such as the PCI procedure discussed below, must generally be used.

Exonuclease digestion is carried out under conditions that are effective to chew-back a sufficient number of nucleotides to allow for specific annealing of the exposed single-stranded regions of homology. In general, at least the entire region of overlap is chewed back, leaving overhangs which comprise the region of overlap. Such an exonuclease digestion is illustrated in FIG. 1. In other embodiments, e.g., when the region of overlap is very long, it may only be necessary to chew-back a portion of the region (e.g., more than half of the region), provided that the single-stranded overhangs thus generated are of sufficient length and base content to anneal specifically under the conditions of the reaction. By "annealing specifically" is meant herein that a particular pair of single-stranded overhangs will anneal preferentially (or only) to one another, rather than to other single-stranded overhangs which are present in the reaction mixture. By "preferentially" is meant that at least about 95% of the overhangs will anneal to the paired overhang. A skilled worker can readily determine the optimal length for achieving specific annealing of a sequence of interest under a given set of reaction conditions. Generally, the homologous regions of overlap (the single-stranded overhangs or their complements) contain identical sequences. However, partially identical sequences may be used, provided that the single-stranded overhangs can anneal specifically under the conditions of the reactions.

A variety of buffers, salts, and energy sources can be used in the chew-back reactions. Some exemplary reaction components are disclosed in the Examples. The digestion reaction is carried out for a period of time that is a function of the size of the overlapping region and the temperature of the reaction. For example, using a T4 DNA polymerase, a 5 minute reaction at about 37° C. is sufficient to chew-back overlaps of about 40-80 bases, and a 15 minute reaction at about 37° C. is sufficient to chew-back overlaps greater than about 300 bases. For Vent/Deep Vent polymerase, an incubation time of about 30 seconds at 65° C. is sufficient to chew-back overlaps of about 40 bases, and about 90 seconds at 65° C. to chew-back overlaps of about 300 bases. In general, the amount of exonuclease activity used is between about 0.1 and about 70 U/ml. (All enzyme units used herein are units as defined by NEB.)

The exonuclease reaction can be terminated by any of a variety of procedures and, at the same time or subsequently, the reaction mixture can be treated to facilitate the annealing of the single-stranded overhangs. In one embodiment, the exonuclease-digested mixture of the first step is terminated with a conventional PCI procedure (as used herein, a "PCI procedure" refers to extraction with phenol/chloroform/isoamyl alcohol, followed by precipitation with ethanol and drying of the pellet by evaporation, such as in a Speed-Vac). "Cleaning up" the DNA mixture in this manner terminates the exonuclease digestion and enhances the efficiency of annealing of the single-stranded overhangs. In fact, in some embodiments, nearly all or all of the annealing of the single-stranded overhangs may occur during the PCI procedure.

In another embodiment of the invention, following the chew-back reaction, the mixture is incubated at an effective temperature, e.g., at 75° C. plus or minus about 5° C., for an effective period of time. The heating step is effective to initiate the annealing reaction and, in some cases, to inactivate the enzyme having an exonuclease activity. In one embodiment, in which a clean-up procedure, such as a PCI procedure, is not required, this heating step is carried out in the presence of a suitable amount of an agent (a crowding agent) that allows for, enhances or facilitates molecular crowding. Without wishing to be bound by any particular mechanism, it is suggested that a crowding agent, which allows for molecular crowding, binds to and ties up water in a solution, allowing components of the solution to come into closer contact with one another. For example, DNA molecules to be recombined can come into closer proximity (even if the reaction components have not been "cleaned up," e.g., by a PCI procedure); this thus facilitates the annealing of the single-stranded overhangs. Also, it is suggested that enzymes can come into closer contact with their DNA substrates and can be stabilized by the removal of water molecules. A variety of suitable crowding agents will be evident to the skilled worker. These include a variety of well-known macromolecules, such as polymers, e.g., polyethylene glycol (PEG 200 and up, including 20,000 and up); Ficoll, such as Ficoll 70; dextran, such as dextran 70; or the like. Much of the discussion in this application is directed to PEG. However, the discussion is meant also to apply to other suitable crowding agents. A skilled worker will recognize how to implement routine changes in the method in order to accommodate the use of other crowding agents.

In general, when PEG is used, a concentration of about 5% (weight/volume) is optimal. However, the amount of PEG can range from about 3 to about 7%. Any suitable size of PEG can be used, e.g., ranging from about PEG-200 (e.g., PEG 4000) to about PEG-20000. In the Examples herein, PEG-8000 was used. In a preferred embodiment of the invention, the PEG is added at the beginning of the recombination reaction (during the exonuclease digestion). Therefore, the exonuclease digestion, heating and slow cooling steps can all be carried out in a single vessel (e.g., tube or vial), for example in a thermocycler, without having to open the vessel to add the PEG for the annealing step. In a preferred embodiment, PEG (e.g., about 5% PEG) is also present during the repair reaction, during which it is believed to enhance ligation. Surprisingly, the present inventors have found that if PEG is present during all of the steps of the recombination reaction, the total amount of recombination is increased dramatically. See, e.g., Example I and FIG. 2.

In some embodiments of the invention, e.g., when the exonuclease activity is provided by T4 DNA polymerase, it may not be necessary to inactivate the exonuclease activity prior to the repair reaction. For example, following the chew-back and annealing reactions, (a) the reaction mixture can be kept at about 4° C. (or, when the reaction mixture is only to be held for about 2-3 hours, at as high as about 22° C.-24° C.) before the repair reaction is begun, and/or (b) dNTPs can be added immediately. These procedures inhibit the 3'→5' exonuclease activity of the T4 DNA polymerase.

Annealing of the single-stranded overhangs may be performed by first incubating the DNA molecules at a suitable temperature (e.g., 75° C. plus or minus about 5° C.). This heating procedure allows single-stranded overhangs which have annealed, either correctly or incorrectly, to come apart. Also, without wishing to be bound by any particular mechanism, it is suggested that heating of the molecules may "unkink" the single-stranded regions and render them more amenable to hybridizing, and/or to initiate the hybridization. Suitable lengths of times for incubating the DNA molecules will be evident to the skilled worker, e.g., at 75° C. plus or minus about 5° C. for about 15-30 minutes, preferably for about 20 minutes. The term "about," as used herein, refers to plus or minus 20%. Thus, "about" 20 minutes includes 16-24 minutes. "About" also refers to plus or minus 20% when referring to lengths of nucleic acids, temperatures, etc. The end points of ranges, as used herein, are included in the range. Following this heating step, the mixture of DNA molecules is slowly cooled, at a suitable rate, for a suitable amount of time, in a suitable buffer, to allow the single-stranded overhangs to anneal to their specific partners. Generally, "slow cooling" is accomplished at about 6° C./minute. Typical slow cooling regimens are shown in the Examples. In general, the reaction mixtures are slowly cooled to room temp (e.g., about 22° C.-24° C.). However, the reaction mixes may be cooled to about 4° C. to facilitate the storage of the reactions until a subsequent step is performed.

When selecting a temperature for incubating (heating) the DNA molecules, the optimal annealing temperature is a function of the melting temperature of the overlap in question. If more than two DNA molecules are to be joined, an investigator should take into account the likelihood of there being multiple temperatures of annealing. To simplify this step, rather than calculating the Tm's for each overlapping sequence, it is preferable, and simpler, to start at the most stringent Tm expected (generally about 75° C.) and to slow cool to about 22° C.-22° C. This should cover all possible Tm's of a wide variety of possible overlaps. If desired, one can slow cool only to the Tm of the smallest value, rather than cooling down to 22° C.-24° C. For example, if the smallest Tm is 50° C., it is only necessary to slow cool to 50° C. Of course, cooling to a lower temperature can be used if it is desirable to store the reaction until a subsequent reaction step is performed. The slow cooling step allows one to anneal a variety of DNA molecules, having overlaps with different Tm's, in a single vessel.

In one embodiment, an annealing-promoting protein is added to the reaction mixture to enhance the annealing of the single-stranded DNA overhangs, and to obviate the need to heat and cool the reaction in order to achieve annealing. That is, the presence of the annealing-promoting protein allows for the reaction to be isothermal. A variety of suitable such proteins will be evident to the skilled worker. These include, e.g., *E. coli* RecA, *E. coli* single-stranded binding protein (SSB), T7 SSB (T7 gene 2.5 product), T4 gene 32 protein, Rac prophage RecT, and lambda phage Redβ. Much of the discussion herein is directed to the use of RecA protein. However, the discussion is meant also to apply to other suitable annealing-promoting proteins. A skilled worker will recognize routine modifications in reaction conditions which can be employed when annealing-promoting proteins other than RecA are used.

Example X shows a typical in vitro recombination procedure, of two DNA molecules, using RecA as an annealing-promoting protein. The method can also be used to generate much larger recombinant molecules, e.g., for the assembly of a gene or genome of interest.

For simplicity, the annealing-promoting protein (for the purposes of this discussion, RecA protein) can be added during the chew-back reaction (e.g., when using T4 DNA polymerase at 37° C.). However, when the enzyme used in the chew-back reaction is incubated at a high temperature (e.g., Vent polymerase), the reaction should generally be cooled to about 37° C. before the RecA protein is added. When the RecA protein is present in the reaction mixture, it is not necessary to raise the temperature and slow cool in order to achieve annealing of the single-stranded overhangs. Thus, when the chew-back and annealing reactions are complete, dNTPs and ligase (and, e.g., a suitable energy source, such as ATP, preferably at a concentration of about 1 mM) can be added directly to complete the recombination procedure without having to heat-inactivate the polymerase beforehand. In one embodiment, when the chew-back reaction is performed at a moderate temperature such as 37° C., ligase may be present in the reaction mixture during the chew-back reaction (instead of adding it back during the repair step). In this embodiment, only the dNTPs need be added to the reaction mixture in order to initiate the repair process. In this embodiment, the energy source (e.g., ATP) can be present throughout the recombination reaction.

Recombination in the presence of an annealing-promoting protein can be carried out under any suitable conditions. For example, as shown in Example X, the NEB DNA ligase buffer may be used during both the chew-back and the repair steps. Alternatively, a buffer comprising 0.2M Tris, pH 7.5 may be used for the chew-back reaction, and a buffer comprising 0.05 M Tris, pH 7.5 for the repair reaction. A crowding agent (e.g., about 5% PEG) may be present during the chew-back and/or the repair reaction. Also, it is preferable that an energy source, such as ATP, preferably at a concentration of about 1 mM, be present for optimal ligase activity.

Many embodiments of the invention can be carried out in a single vessel (e.g., tube or vial). This can be accomplished, e.g., in embodiments in which the exonuclease activity is terminated with a heating step. In such embodiments, a PCI "clean-up" procedure, which requires transfer of solution to a second vessel, is not required. Furthermore, the inventors have identified a buffer system (buffers and other reaction components) which, although it may not be optimal for each of the enzymes used, allows each of the enzymes to be sufficiently active to carry out a method of the invention. Thus, it is not necessary to change buffers between steps by transferring the reagents to a new tube. This buffer system is discussed in more detail below.

Following the annealing steps, the single-stranded gaps left by the exonuclease (see FIG. 1) are filled in with a suitable DNA polymerase (sometimes referred to herein as a "polymerase") and the nicks thus formed are sealed with a ligase which is compatible with the DNA polymerase. The type of DNA polymerase used is a function of, among other factors, whether the 5' ends of the DNA molecules to be repaired are phosphorylated. In general, between about 10 and about 130 (e.g., between about 30 and about 50) U/ml (unit defined by NEB) of DNA polymerase are used in each reaction.

Generally, a DNA polymerase used for the repair step of a method of the invention is a non-strand-displacing DNA polymerase. The enzyme may or may not have a nick-translating activity. A "non strand-displacing DNA polymerase," as used herein, is a DNA polymerase that terminates synthesis of DNA when it encounters DNA strands which lie in its path as it proceeds to copy a dsDNA molecule, or that degrades the encountered DNA strands as it proceeds while concurrently filling in the gap thus created, thereby generating a "moving nick" (nick translation).

In some embodiments of the invention, the DNA polymerase has nick-translation activity. In order for a first DNA molecule to be ligated to the 3'-OH group of another DNA molecule, the first DNA molecule must have a 5' phosphorylated end. A DNA polymerase which has a nick-translation activity creates 5'-ends that are phosphorylated and thus are able to be ligated. Therefore, polymerases with nick-translating activity can be used in methods of the invention with DNA molecules which either have or do not have 5' phosphorylated ends. Taq polymerase or E. coli DNA polymerase holoenzyme are among the suitable DNA polymerases of this type. An advantage of using a polymerase with a nick-translating activity for this step is that it is not necessary to phosphorylate the 5' end of the DNA molecule, thus saving the time and cost of phosphorylating the molecules. Furthermore, such an enzyme can be used to remove unwanted restriction enzyme recognition sites via its nick-translation activity (see Example VI and FIG. 6).

In another embodiment, the DNA polymerase does not have a nick translating activity. Such a polymerase is effective only in cases in which the 5' ends are phosphorylated. T4 DNA polymerase, T7 DNA polymerase, Phusion™ polymerase, and Pfu polymerase (when used below about 68° C.) are among the suitable DNA polymerases of this type. If the DNA molecules to be joined are not phosphorylated (e.g., are prepared by PCR amplification), the following procedures can be used to allow DNA polymerases lacking nick translation activity be used in the repair reaction: (a) generate the DNA molecules to be joined by PCR, by using PCR primers which have been phosphorylated prior to the PCR, or (b) phosphorylate the 5'-ends using T4 polynucleotide kinase and ATP during the chew-back reaction.

Reaction components (such as salts, buffers, a suitable energy source (such as ATP or NAD), pH of the reaction mixture, etc.) can be optimized for each of the steps of the method. However, to reduce the number of manipulations and to avoid having to change buffers for the exonuclease, annealing and repair reactions, it is preferable to carry out the entire recombination procedure under essentially the same reaction conditions. In some embodiments, the buffers, etc., are not optimal for any of the reactions, but can serve as a compromise that is effective for the entire set of reactions. Some exemplary reaction conditions are presented in the Examples. For example, in one embodiment, the chew-back and annealing reactions are carried out in a solution that comprises about 0.2 M Tris-Cl, pH 7.5 and about 5% PEG (as well as other components, such as BSA, about 10 mM $MgCl_2$, and DTT). Following completion of the chew-back and annealing reactions, the reaction mixture is diluted 1:4, which reduces the concentration of Tris to 0.05M, and PEG is added to a final concentration of about 5%. Other ingredients may also be added to the repair mixture, e.g., dNTPs, $MgCl_2$ to a final concentration of about 10 mM, DTT, an energy source for the ligase (such as NAD or ATP), and the enzymes for the repair reaction (polymerase and ligase). Surprisingly, the inventors have found that the use of a high concentration of Tris at pH 7.5 in the chew-back/annealing reaction, and/or the presence of about 5% PEG in all steps of the recombination, reaction provide superior overall results compared to conditions recommended by the manufacturers of the enzymes used in the procedure.

The nicks generated by the gap-filling reaction can be sealed with any of a variety of suitable DNA ligases (sometimes referred to herein as "ligases"). Among the suitable ligases are, for example, phage T4 DNA ligase, E. coli DNA ligase, Taq DNA ligase, Ampligase®, or the phage T7 gene 1.3 product. In general, about 1/10 volume of ligase is added. Thus, the final concentration of ligase in the reaction mixture is generally about 40 U/µl of T4 ligase, about 4 U/µl of Taq ligase, or about 1 U/µl of E. coli DNA ligase. Preferably, the repair reactions are carried out with a polymerase and a ligase that are compatible, and can be used simultaneously. That is, the two enzymes can be incubated under conditions which are suitable for both enzymes. Typical examples include: repair with Taq DNA polymerase, Taq DNA ligase, and an energy source, such as NAD, at about 45° C. (e.g., for about 15 minutes), in a reaction mixture such as that described in Example IX; or incubation with *E. coli* DNA polymerase I and T4 DNA ligase, and an energy source, such as ATP, at about 37° C. (e.g., for about 15 minutes), in a reaction mixture such as that described in Example VIII. Other combinations will be evident to the skilled worker. For example, because Taq polymerase exhibits some activity at 37° C., it may be paired with a ligase that functions at 37° C.

The reaction conditions are selected so that the ligation activity is greater than the polymerase activity. For example, the inventors have found, surprisingly, that when using Taq DNA polymerase and Taq DNA ligase, it is optimal to incubate the reaction at about 45° C. (rather than 65° C. or 75° C., which are optimal for the ligase and the polymerase, respectively); incubation at 45° C. results in a balance of the enzymatic activities in favor of the ligation reaction. The inventors have also found that, when setting up such a repair reaction, it is preferable to place the reaction components at 4° C. (e.g., on ice). If this is not done, and the reaction mixture is allowed to sit at room temperature for as short a time as one or two minutes, the Taq polymerase will begin filling in the gaps and disrupting the complex before the Taq ligase has had a chance to function. If the reaction is performed in a thermocycler, it may be convenient to slow cool the chew-back/annealing reaction to 4° C., then to add cold (e.g., 4° C.) repair reaction. The thermal cycler can then be set at about 45° C. once all the components have been added.

In one embodiment, substantially all of the nicks (or all of the nicks) are sealed during the reaction procedure. However, in one embodiment, joined DNA which still comprises some nicks is transformed into a bacterium, such as *E. coli*, and the nicks are sealed by the bacterial machinery.

In one embodiment of the invention, the entire procedure is carried out as a "one-step" reaction (in a single tube, which does not have to opened during the entire recombination procedure, in a thermocycler apparatus). In one such procedure, a mixture of the DNAs to be joined is incubated at 37° C. with exonuclease III; RecA, or a comparable protein, such as an SSB; Taq DNA polymerase; Taq DNA ligase; dNTPs and a buffer compatible with all of these enzymatic activities. Because the Taq enzymes are not very active at 37° C., the exonuclease III prevails, and chew-back and annealing reactions occur during this incubation. The temperature is then raised to 55° C. The exonuclease III is inactive at this temperature, so the repair reactions can occur.

As used herein, the singular forms "a," "an," and "the" include plural referents unless the context clearly dictates otherwise.

The term, an "isolated" protein, as used herein, means that the protein is removed from its original environment (e.g., the natural environment if it is naturally occurring), and isolated or separated from most other component with which it is naturally associated. For example, a naturally-occurring protein present in its natural living host (e.g., a bacteriophage protein present in a bacterium that has been infected with the phage) is not isolated, but the same protein, separated from some or all of the coexisting materials in the natural system, is isolated. Such proteins can be part of a composition or reaction mixture, and still be isolated in that such composition or reaction mixture is not part of its natural environment. The term "an isolated protein," as used herein, can include 1, 2, 3, 4 or more copies of the protein, i.e., the protein can be in the form of a monomer, or it can be in the form of a multimer, such as dimer, trimer, tetramer or the like, depending on the particular protein under consideration. In some embodiments, the protein is purified. Methods for purifying the proteins used in methods of the invention are conventional. In some embodiments, the protein is substantially purified or is purified to homogeneity. By "substantially purified" is meant that the protein is separated and is essentially free from other proteins, i.e., the protein is the primary and active constituent. The purified protein can then be contacted with the DNAs to be joined. Proteins used in the methods of the invention can be in the form of "active fragments," rather than the full-length proteins, provided that the fragments retain the activities (enzymatic activities or binding activities) required to achieve the joining. One of skill in the art will recognize how to make and use such active fragments.

Methods of the invention are generally carried out in vitro. That is, all of the protein components are isolated and/or substantially purified. The in vitro recombination reactions are not carried out in a living cell or with a crude cell extract; the reactions are carried out in a cell-free environment.

In methods of the invention, a plurality of DNA molecules are contacted with the enzymes under conditions effective to join the DNA molecules to form a substantially intact (preferably having no nicks) double-stranded DNA molecule (e.g., in which a single copy of the region of sequence identity is retained).

DNA molecules of any length can be joined by methods of the invention. The minimum size for joining molecules with a 40 by overlap is about 80 bp. For molecules with a 200 by overlap, the minimum size is about 400 bp. Theoretically, there should be no maximum size of DNA molecules that can be joined (although very large molecules would be more fragile than smaller ones, and thus subject to possible breakage). For example, cassettes having about 100 by to about 300 kb (or greater) can be joined. The Examples show, e.g., the joining of two DNA molecules of ~24 kb each.

From two to an essentially unlimited upper level of DNA molecules can be joined. In general, at least about 10 fragments can be joined. The number of fragments which can be joined depends, in part, on the length of the overlaps and the lengths of the fragments. For example, with fragments having overhangs of about 150 to about 200 by (e.g., fragments of about 3 kb, or larger or smaller), the number of fragments that can be joined is substantially unlimited. The number of fragments that can be joined in one reaction also depends, in part, on the efficiency of the joining process. If the efficiency of joining is 100%, then an infinite number of DNA molecules could theoretically be joined (provided that an approximately equal number of molecules of each substrate is present in the reaction). With lower efficiencies (e.g., about 75-90% joining of each pair of two molecules), two to about 250 DNA molecules can be joined. Methods of the invention work well with a wide range of substrate DNA (e.g., about 10 to about 1000 ng of each substrate in a reaction mixture.)

In some embodiments of the invention, the joined DNA molecules form a circle and/or become ligated into a vector to form a circle. The lower size limit for a dsDNA to circularize is about 200 base pairs. Therefore, the total length of the joined fragments (including, in some cases, the length of the vector) is preferably at least about 200 by in length. There is no practical upper size limit, and joined DNAs of a few hundred kilobase pairs, or larger, can be generated by a method of the invention. The joined DNAs can take the form of either a circle or a linear molecule.

More particularly, the number of DNA molecules or cassettes that may be joined in vitro to produce an end product, in one or several assembly stages according to the invention, may be at least or no greater than about 2, 3, 4, 6, 8, 10, 15, 20, 25, 50, 100, 200, 500, 1000, 5000, or 10,000 DNA molecules, for example in the range of about 4 to about 100 molecules. The number of assembly stages may be about 2, 4, 6, 8, 10, or more. The number of molecules assembled in a single stage maybe in the range of about 2 to about 10 molecules. The methods of the invention may be used to join together DNA molecules or cassettes each of which has a starting size of at least or no greater than about 80 bs, 100 bs, 500 bs, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of about 3 kb to about 500 kb. The DNA end products of the inventive methods maybe at least about 500 bs, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of 30 kb to 1 Mb. As described in Example IV, the inventive methods maybe used for in vitro assembly of about 100 cassettes of about 6 kb each, into a DNA molecule of about 600 kb.

When joining a mixture of DNA molecules, it is preferable that the DNAs be present in approximately equimolar amounts. If the number of DNA molecules is not balanced, the result would be a termination of assembled species. For example, consider an example in which 8 DNA molecules are to be assembled (numbered 1-8). If, for example, there was an excess of molecule number 4, the majority of assembled molecules would be 1-4 and 4-8. Assuming only a few hundred bases is being chewed back in the reaction, there would be no sequence homology between the distal region of 1-4 and the proximal region of 4-8, thereby decreasing the amount of 1-8.

In methods of the invention, the distal region of one of a pair of dsDNA molecules to be joined shares a region of sequence homology (e.g., sequence identity) with the proximal region of the other dsDNA molecule. The term "distal" as used herein refers to the 3' end of a first DNA molecule of a pair to be joined (the 5'-most DNA molecule), and the term "proximal" refers to the 5' end of the second DNA molecule of the pair. The regions of homology are sometimes referred to herein as "overlaps" or "regions of overlap." FIG. 1 shows a schematic representation of the distal and proximal regions of DNA molecules to be joined. A "region of sequence homology (identity)", as used herein, refers to both strands of the double-stranded DNA molecule. Thus, one strand from this region can hybridize specifically to its complementary strand, e.g., when the complementary regions are present in single-stranded overhangs from the distal and proximal regions of the two molecules to be joined.

The region of sequence identity should be sufficiently long to allow specific recombination to occur. That is, it should be long enough so that the region of overlap at the ends of two DNA molecules to be joined is unique to those DNA molecules, and no other DNA molecules will anneal to those two DNA molecules during the recombination reaction. The length can vary from a minimum of about 10 base pairs (bp) to about 300 by or more. For relatively short overlaps (e.g., up to about 40 or 60 nt), it is preferable that the sequences be non-palindromic. In general, it is preferable that the length of the overlap is less than or equal to about % Z the size of the fragment to be combined, but not less than about 10 by and not more that about 1000 bp. For the joining of 2 or 3 fragments, about 20-30 non-palindromic by overlap may be sufficient. For more than 10 fragments, a preferred overlap is about 80 by to about 300 bp. In one embodiment, the region of sequence identity is of a length that allows it to be generated readily by synthetic methods, e.g., about 40 by (e.g., about 32 to about 48 bp). The overlaps maybe, e.g., about 10, 20, 30, 40, 50, 60, 70, 80, 90, 100, 150, 200, 250, 300, 350, 400, 450, 500, 550, 600, 650, 700, 750, 800, 850, 900, 950 or 1,000 nt in length.

In a preferred embodiment, when a plurality of DNA molecules are to be joined, for each pair of DNA molecules to be joined, the distal region of one of the DNA molecules of the pair is designed to share a region of sequence identity with the proximal region of the other DNA molecule of the pair, and the distal and proximal regions of sequence identity for each pair of DNA molecules are designed to be unique (to be different from the regions of sequence identity of the other pairs of DNA molecules). When the overlapping regions of identity are designed in this manner, the orientation and order of the DNA molecules in the joined molecule can be predetermined A number of DNA molecules (for example, 4 or 6 molecules) can thus be incubated together in a single reaction mixture (in a single vessel or container) in a method of the invention, and be joined into a longer DNA molecule in which the individual DNAs are arranged in any desired order and orientation.

The regions of sequence identity present in the proximal and distal regions of the DNAs to be joined can be generated by any of a variety of methods.

For example, in one embodiment of the invention, synthetically prepared, overlapping fragments of a gene or genome of interest (e.g., about 5-6 kb in length, or longer or shorter) are optionally amplified (e.g., by PCR, or by MDA such as a rolling circle mechanism) and are joined by a method of the invention in the order and orientation in which they are located in the gene or genome. In this method, the first DNA fragment (e.g., in the 5' most portion of the gene or genome) is synthesized so that the region at its 3' end (the distal end) contains a sequence (e.g., about 40 bp) that is identical to the sequence at the 5' end (the proximal end) of the DNA fragment to which it is to be joined. The second DNA fragment, in turn, is synthesized so that it has, at its distal end, a sequence which is identical to the sequence at the proximal end of the third DNA fragment, and so on. In another embodiment, synthetically prepared fragments of a gene or genome of interest are inserted into a vector, propagated in *E. coli* to make more of the synthetically prepared fragment, then released from the vector, optionally amplified further by PCR, MDA or RCA, and joined by a method of the invention in the order and orientation in which they are located in the gene or genome. These procedures allow the preparation of a synthetic gene or genome.

In another embodiment of the invention, two fragments to be joined are generated by restriction enzyme digestion, such that the fragments overlap one another, e.g., by about 20 to about 1000 bp. The overlapping regions can then be joined by a method of the invention. Greater numbers of fragments can also be generated by these methods and joined. Combinations of the preceding method and methods using synthetically prepared DNA molecules and/or molecules generated by PCR can be used.

In embodiments of the invention, the regions of identity are introduced by PCR amplification.

In one such method, a fragment of interest is inserted into a vector. For example, a plasmid vector can be linearized with a restriction enzyme, generating a sequence A (e.g., having 40 bp) to the left of the restriction enzyme cut and a sequence B (e.g., having 40 bp) to the right of the restriction enzyme cut. The fragment to be cloned into the vector is PCR amplified, using PCR primers which will introduce sequence A at the left end of the fragment, and sequence B at the right end of the fragment. The regions of sequence identity (in this example, each having 40 bp) allow the fragment to be joined to the vector in a desired orientation, to form a circular molecule. Alternatively, particularly when it is desirable to avoid errors which might be introduced into an insert during PCR amplification, the vector can be PCR amplified in order to introduce at the ends of a cloning site sequences which overlap sequences at the ends of the insert. The methods described above allow for the directional cloning of any insert of interest, without having to rely on the presence of, or introduction of, restriction enzyme sites on the insert.

In a variation of the preceding method, two or more (e.g., three or more) DNA fragments are joined to one another to form a linear molecule. In this variation of the preceding method, regions of sequence identity that are unique to each pair of fragments to be joined are introduced into the fragments by PCR amplification, using suitable primers. For each DNA fragment to be joined to another fragment, a sequence is introduced to the 3' (distal) end of the first fragment which overlaps with the sequence at the 5' (proximal) end of the fragment to which it is to be joined. As in the preceding method, PCR primers are used in which the regions of sequence identity (e.g., 40 nt) lie 5' to a PCR primer (e.g., having 20 nt). After a suitable number of rounds of PCR amplification, DNA fragments are produced in which defined regions of sequence identity are present at the ends of the fragments. The resulting fragments can then be joined in a predetermined order and orientation by a method of the invention.

If desired, the joined, linear DNA fragments may be circularized, or they may be inserted into a vector to form a circle (simultaneously with the joining of the fragments, or subsequent to that joining). For example, a vector can be present in the joining reaction, so that the joined fragments are introduced into the vector. The efficiency of joining a large number of fragments (e.g., 6 or 8 fragments) into a vector by a method of the invention is greater than when using a method which employs compatible restriction enzyme sites. In a typical cloning experiment with restriction enzymes and T4 DNA ligase, probability is not in favor of the researcher getting multiple inserts to ligate into a vector. However, in the assembly methods of the invention, a researcher can join about 6 inserts into a vector with approximately 20-50% efficiency, or greater. Furthermore, since the efficiency is high, there is an increased ratio of recombinants to non-recombinants. The background level of non-recombinants can be reduced further by isolating a pure band by agarose gel electrophoresis (since this method produces a high enough yield to isolate a band on agarose gels) or with a sizing column. A DNA of the desired size (having the correct number of joined DNA molecules) can be isolated and introduced into a vector, e.g., using a method of the invention. If the final product is a circle, there is no need to isolate it by agarose gel electrophoresis. Rather, the sample can be treated with an enzyme such as Plasmid-Safe (Epicentre), an ATP-dependent DNAse that selectively hydrolyzes linear dsDNA but not circular dsDNA. If the user's application does not require a pure clone, there may be a sufficient amount of DNA without the need to transform into *E. coli* and do plasmid preparations.

In one embodiment, joined DNA molecules and/or DNA molecules inserted into vectors are introduced into a host cell, such as a bacterial or eukaryotic cell (e.g., by transformation or transfection). Alternatively, the reaction mixture comprising the joined DNA molecules can be introduced into a host cell; only those DNAs which have recombined to form circular molecules can survive in the host cell. In another embodiment, the joined fragments and/or fragments inserted into vectors are used directly, without further passage through a cell, such as a bacterial cell.

Molecular biology methods of the invention can be carried out using conventional procedures. See, e.g., discussions in Sambrook, et al. (1989), *Molecular Cloning, a Laboratory Manual*, Cold Harbor Laboratory Press, Cold Spring Harbor, N.Y.; Ausubel, et al. (1995). *Current Protocols in Molecular Biology*, N.Y., John Wiley & Sons; Davis, et al. (1986), *Basic Methods in Molecular Biology*, Elseveir Sciences Publishing, Inc., New York; Hames, et al. (1985), *Nucleic Acid Hybridization*, IL Press; Dracopoli, et al. (current edition) *Current Protocols in Human Genetics*, John Wiley & Sons, Inc.; and Coligan, et al. (current edition) *Current Protocols in Protein Science*, John Wiley & Sons, Inc.

A variety of uses for the inventive method will be evident to the skilled worker. The inventive method can be substituted for any method in which restriction enzyme digests are used to generate compatible sequences for joining DNA molecules. In one embodiment of the invention, DNA molecules that are too large to be amplified by PCR can be cloned by joining sub-fragments by a method of the invention and then inserting them into a suitable vector. Some pieces of DNA are unstable (and therefore, unclonable) in *E. coli*, especially those that are high in A+T % content. A method of the invention allows for the assembly of DNA in vitro without the need to be transformed into *E. coli*. Furthermore, Phi29 DNA polymerase can be added to the reaction to amplify the circular DNA. An in vitro recombination system of the invention can be used to recombine any homologous DNAs of interest, e.g., to repair double-stranded DNA breaks or gaps, etc. Another application of the method is to introduce a mutation into a DNA. In this method, a mutation is introduced into both the upper and lower strand PCR primers, so the amplified fragments are 100% mutant; then the fragments are joined by the method of the invention.

One embodiment of the invention is to join cassettes, such as the 5-6 kb DNA molecules representing adjacent regions of a gene or genome of interest that are described in the Examples, to create combinatorial assemblies. For example, it may be of interest to modify a bacterial genome, such as a putative minimal genome or a minimal genome, so that one or more of the genes is eliminated or mutated, and/or one or more additional genes is added. Such modifications can be carried out by dividing the genome into suitable cassettes, e.g., of about 5-6 kb, and assembling a modified genome by substituting a cassette containing the desired modification for the original cassette. Furthermore, if it is desirable to introduce a variety of changes simultaneously (e.g., a variety of modifications of a gene of interest, the addition of a variety of alternative genes, the elimination of one or more genes, etc.), one can assemble a large number of genomes simultaneously, using a variety of cassettes corresponding to the various modifications, in combinatorial assemblies. After the large number of modified sequences is assembled, preferably in a high throughput manner, the properties of each of the modified genomes can be tested to determine which modifications confer desirable properties on the genome (or an organism comprising the genome). This "mix and match" procedure produces a variety of test genomes or organisms whose properties can be compared. The entire procedure can be repeated as desired in a recursive fashion.

The disclosed methods can be used to join any nucleic acid molecules of interest. The nucleic acid molecules can come from any source, including a cellular or tissue nucleic acid sample, cloned fragments or subclones thereof, chemically synthesized nucleic acids, genomic nucleic acid samples, cDNAs, nucleic acid molecules obtained from nucleic acid libraries, etc. The DNAs can be radioactively labeled or can comprise binding entities, such as biotinylated nucleotides, which can aid in the purification of the joined DNAs. If desired, the DNA molecules to be joined, or primers for adding overlapping regions of sequence identity, can be prepared synthetically. Conventional synthesis techniques include using phosphoroamidite solid-phase chemistry to join nucleotides by phosphodiester linkages. Chemistry for joining nucleotides by phosphorothioate linkages or different linkages, such as methylphosphonate linkages, can also be used. For example, the cyanoethyl phosphoramidite method can be used, employing a Milligen or Beckman System 1 Plus DNA synthesizer (for example, Model 8700 automated synthesizer of Milligen-Biosearch, Burlington, Mass. or ABI Model 380B). Synthetic methods useful for making DNA molecules are also described by Ikuta, et al., *Ann Rev. Biochem.* (1984) 53:323-356, (phosphotriester and phosphite-triester methods), and Narang, et al., *Methods Enzymol.* (1980) 65:610-620 (phosphotriester method). DNAs prepared by methods as above are available from commercial sources, such as Integrated DNA Technologies (IDT), Coralville, Iowa.

Methods of the invention are amenable to automation and to adaptation to high throughput methods, allowing for the joining of multiple DNA molecules simultaneously by computer-mediated and/or robotic methods that do not require human intervention.

Any combination of the materials useful in the disclosed methods can be packaged together as a kit for performing any of the disclosed methods. For example: an enzyme having a 3' or 5' exonuclease activity; a non strand displacing DNA polymerase; a ligase which is compatible with the polymerase; and, optionally, a protein which enhances the annealing of single-stranded DNAs can be packaged individually or in various combinations. Sufficient amounts of these protein reagents for many reactions may be present in a single vial, and aliquots may be removed for individual reactions; or the proteins may be packaged in amounts suitable for a single use. In one embodiment, the polymerase and the ligase are packaged together. In another embodiment, a polymerase (which serves as either an exonuclease or a polymerase, if dNTPs are absent or present, respectively); a protein which enhances annealing, such as RecA or an SSB protein; and a ligase are packaged together. In another embodiment, suitable for use in an isothermal, single tube procedure, a 3' exonuclease; a protein which enhances annealing, such as RecA or an SSB protein; Taq DNA polymerase; and Taq DNA ligase are packaged together. Other combinations of proteins for implementing methods of the invention will be evident to the skilled worker. If desired, the protein reagents can be packaged in single use form, suitable for carrying out one set of DNA joining reactions. The protein reagents of the kit may be in containers in which they are stable, e.g., in lyophilized form or as stabilized liquids. In one embodiment, the proteins are stored as solutions in 50% glycerol.

Optionally, kits of the invention comprise instructions for performing the method. Other optional elements of a kit of the invention include suitable buffers, packaging materials, etc. Reaction components, such as buffers, salts, PEG or the like, which have been optimized for one or more of the enzymatic reactions, can be included, in a concentrated or a dilute form, along with the enzymes or packaged separately from them. For example, PEG at a final concentration of about 5%, or a concentrated solution that can be diluted to this concentration, can be present in a kit of the invention. Also, or alternatively, about 0.2 M Tris pH 7.5, or a concentrated solution that can be diluted to this concentration, can be included in the kit.

A kit of the invention may include one or more separately packaged solutions with components that are suitable for methods of the invention. In one embodiment, the kit contains a first solution, suitable for a chew-back/annealing reaction, which comprises PEG (which, after the addition of other components of the reaction, will reach a final concentration of about 5%), and/or a Tris buffer (which, after the addition of other components of the reaction, will reach a final concentration of about 0.2 M Tris, at about pH 7.5), to which can be added the DNA molecules to be joined and an enzyme having an exonuclease activity (such as T4 DNA polymerase). This first solution can also include other ingredients, such as $MgCl_2$, DTT, BSA, etc. In one embodiment, the kit also contains a second solution, suitable for a repair reaction, which comprises PEG (which, after the addition of other components of the reaction, will reach a final concentration of 5%). This solution can also contain water (which, after the addition of other ingredients, including the chewed-back/annealed DNAs and suitable enzymes for a repair reaction, will bring the final concentration of Tris pH 7.5 to 0.05 M), and other ingredients such as $MgCl_2$, DTT, dNTPs, an energy source for ligase (such as NAD or ATP), etc. To this second solution can be added the reaction mixture which contains the chewed-back/annealed DNAs, and the enzymes for a repair reaction (a polymerase and a compatible ligase). For further guidance as to components which can be present in kits, see the reaction mixtures shown in the Examples.

In one embodiment, the kit comprises two vials: the first vial contains a suitable enzyme having exonuclease activity (e.g., T4 polymerase), in a solution containing PEG and other elements required for optimal exonuclease and annealing activity; and the second vial contains a suitable polymerase for the repair reaction (e.g., Taq DNA polymerase), a compatible ligase (e.g., Taq DNA ligase), in a solution containing PEG, a suitable amount of dNTPs, and other elements required for optimal repair activity. With such a kit, the DNAs to be joined are mixed with the contents of the first vial and incubated as described for the chew-back and annealing reactions; then the contents of the second vial are added and the mixture is incubated as described for the repair reaction.

Another aspect of the invention is a composition comprising
 (a) an isolated enzyme which, under suitable reaction conditions (such as the absence of added dNTPs) exhibits a 3' or 5' exonuclease activity (e.g., T4 DNA polymerase);
 (b) a non strand-displacing DNA polymerase (e.g., Taq DNA polymerase); and
 (c) a DNA ligase which is compatible with the DNA polymerase in (b) (e.g., Taq DNA ligase). A composition as above can be present, for example, in a reaction mixture in which a plurality of DNA molecules are being joined by a method of the invention.

DNA used in a method of the invention can be modified in any of a variety of ways, provided that the modified DNA is able to function in the method. A skilled worker can readily determine if a particular modification allows the modified DNA to function (e.g., to be recognized by and acted upon by enzymes used in the method).

DNAs used in methods of the invention can have one or more modified nucleotides. For example, they may contain one or more modifications to either the base, sugar, or phosphate moieties. Modifications to the base moiety would include natural and synthetic modifications of A, C, G, and T as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch, et al. (1991) *Angewandte Chemie, International Edition* 30, 613, and Sanghvi, Y. S., Chapter 15, *Antisense Research and Applications*, pages 289-302, Crooke, S. T. and Lebleu, B. ed., CRC Press, 1993. Certain nucleotide analogs, such as 5-substituted pyrimidines, 6-azapyrimidines and N-2, N-6 and 0-6 substituted purines, including 2-aminopropyladenine, 5-propynyluracil and 5-propynylcytosine. 5-Methylcytosine can increase the stability of duplex formation. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' Sugar modifications also include but are not limited to —O[(CH$_2$)nO]mCH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON[(CH$_2$)nCH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$, CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

It is understood that nucleotide analogs need only contain a single modification, but may also contain multiple modifications within one of the moieties or between different moieties.

Nucleotide substitutes are nucleotides or nucleotide analogs that have had the phosphate moiety and/or sugar moieties replaced. Nucleotide substitutes include molecules having similar functional properties to nucleotides, but which do not contain a phosphate moiety, such as peptide nucleic acid (PNA). Nucleotide substitutes include molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate back-bones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules. See also Nielsen, et al., *Science* (1991) 254:1497-1500.

DNA molecules of the invention can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O- methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can be comprised of bases (that is, the base portion of the nucleotide) and can comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

Another aspect of the invention is an in vitro method to join two or more single-stranded (ss) DNA molecules (e.g., ssDNA oligonucleotides), which is similar to the methods discussed above except, because the molecules are already single-stranded, the "chew-back" step is not necessary. That is, the single-stranded molecules are annealed and then repaired. Chemically synthesized oligonucleotides, from about 20 by to any size that can be synthesized chemically, can be used. For example, 10 ssDNA oligos of about 60 bp, having about 10 by homology overlap at each end, can be assembled simultaneously into a vector. The assembly of 10 such oligonucleotides results in a DNA molecule of about 500 bp. DNA molecules assembled by this method can, in turn, be joined to one or more other DNA molecules assembled by this (or another) method (for example, as in the preceding case, assemblies of about 500 bp). Repetitions of the method can generate very large molecules of DNA; there is no theoretical limit to the size of a DNA molecule thus generated. The enzymes, buffers, and other reaction conditions described above for the "chew-back/annealing/repair" method can be applied to the present method.

In the foregoing and in the following example, all temperatures are set forth in uncorrected degrees Celsius; and, unless otherwise indicated, all parts and percentages are by weight.

EXAMPLES

Example I

Figure 2:
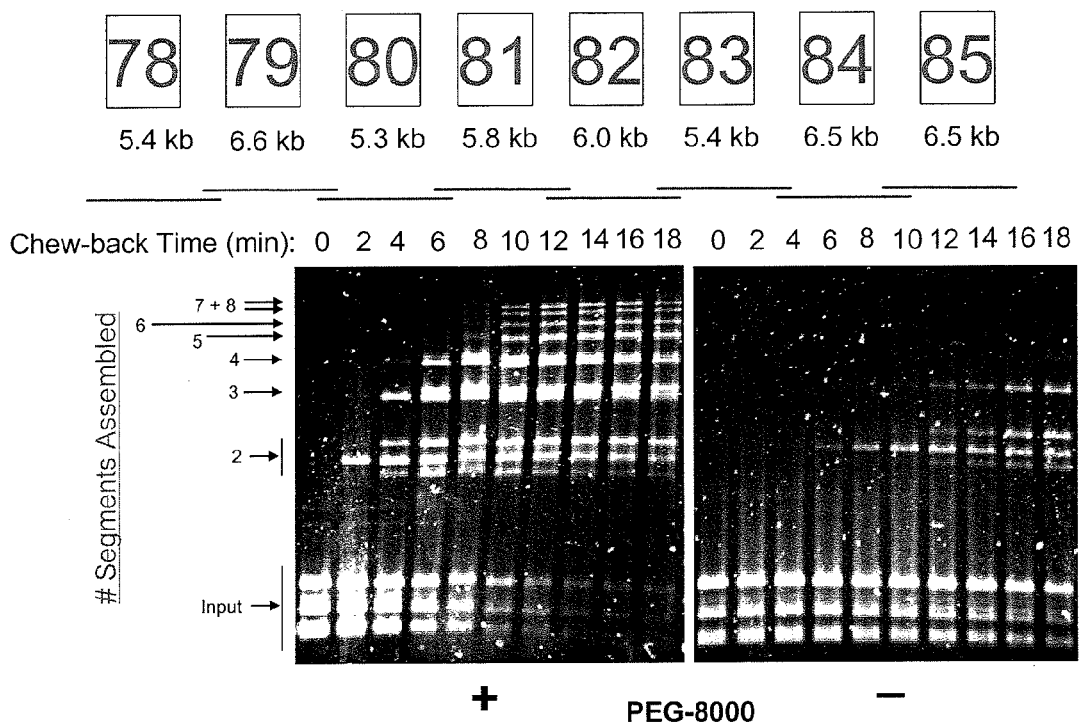
FIG. 2 shows the joining of eight DNA molecules, each about 6 kb with approximately 300 by overlaps, with varying amounts of "chew-back," in the presence or absence of PEG.

Assembly of Eight DNA Molecules, Each having a Length of about 6 kb; the Effect of PEG Eight DNA molecules, having lengths of about 6 kb, and overlaps of about, on average, about 300 bp, were joined. These molecules represent adjacent segments of the *M. genitalium* chromosome. (a) The eight molecules were incubated together with 60 U/ml of T4 DNA polymerase for times ranging from 0 minutes to 18 minutes at 37° C., in an optimized buffer (5% PEG-8000, 10 mM MgCl$_2$, 200 mM Tris-Cl pH 7.5, 1 mM DTT, 1 µg/ml BSA), to create single-stranded overlaps. (b) The single-stranded overlaps were annealed by incubating at 75° C. for 20 minutes, slow cooling at 6° C./minute to 60° C., holding at 60° C. for 30 minutes, then slow cooling at 6° C./minute to 4° C. (c) The gaps and nicks were repaired by adding the 4 dNTPs to a concentration of 200 µM each, Taq DNA polymerase (31.25 U/ml), Taq DNA ligase (4 U/µl) in an optimized buffer (25 µg/ml BSA, 5% PEG-8000, 50 mM Tris-Cl pH 7.5, 10 mM MgCl$_2$, 10 mM DTT, 200 µM each dNTP, 1 mM NAD, 4 U/µl Taq DNA ligase, and 0.03125 U/λ Taq DNA polymerase), and incubating for 15 minutes at 45° C. Parallel reactions were carried out in which PEG-8000 was replaced by water. The reaction mixtures, following chew-back and annealing but before repair, were subjected to gel electrophoresis, along with molecular weight markers. FIG. 2 shows that the assembly reactions were substantially more efficient in the presence of PEG. In the presence of PEG, bands corresponding to the assembly of all eight DNA molecules were evident after 8 minutes of "chew-back"; the percentage of assembled molecules increased after 10 minutes of chew-back, and remained constant to up to 18 minutes of chew-back.

Example II

Figure 3:
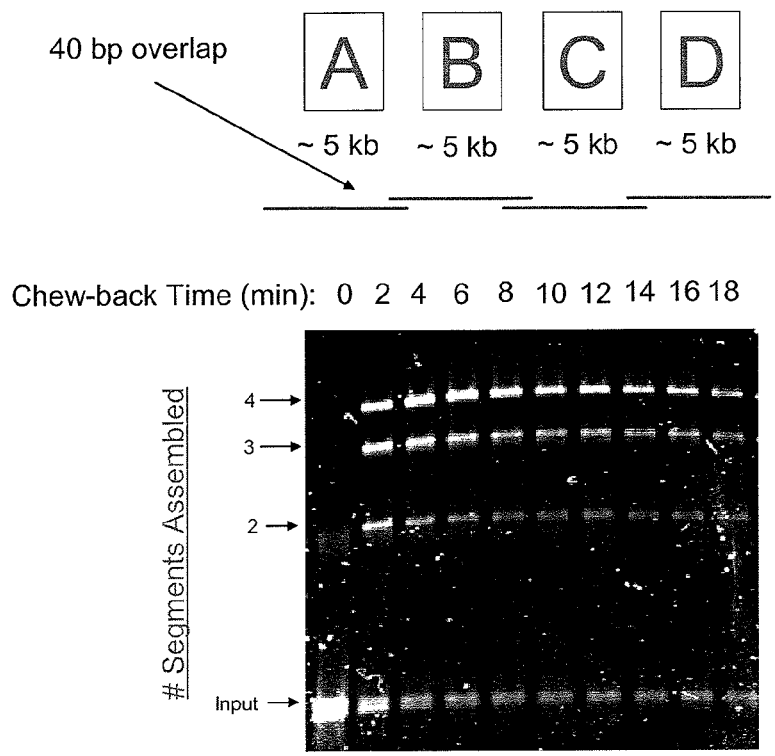
FIG. 3 shows the joining of four DNA molecules, each about 5 kb with 40 by overlaps with varying amounts of "chew-back."

Assembly of Four DNA Molecules with 40 by Overlaps, Each DNA having a Length of About 5 kb Four DNA molecules, with 40 kb overlaps, each DNA having a length of about 5 kb, were joined, using the method described in Example I in which PEG-8000 was present. These molecules represent adjacent segments of the *C. cellulolyticum* chromosome. FIG. 3 shows that significant amounts of assembly of all four DNA molecules were evident after 2 minutes of chew-back.

Example III

Figure 4:
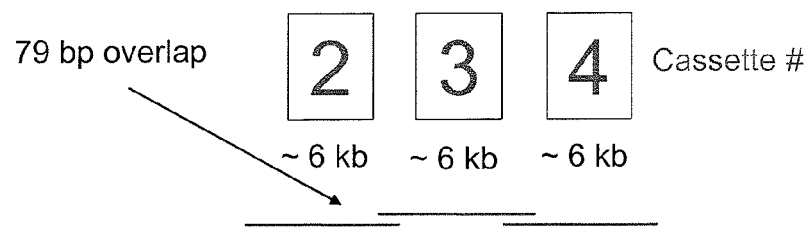
FIG. 4 shows the joining of three DNA molecules, each about 6 kb with 79 by overlaps with varying amounts of "chew-back."
Figure 4:
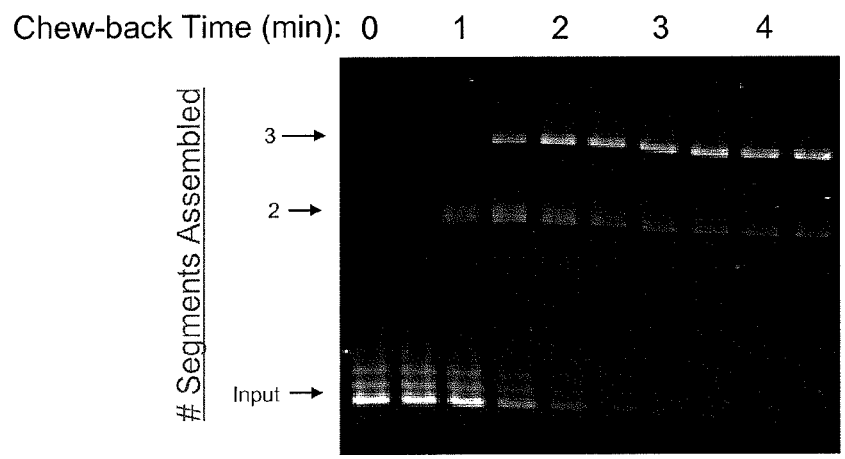

Assembly of Three DNA Molecules with 79 by Overlaps, Each DNA having a Length of About 6 kb Three DNA molecules, with 79 by overlaps, each DNA having a length of about 6 kb, were joined, using the method described in Example I in which PEG-8000 was present. These molecules represent adjacent segments of the *M. genitalium* chromosome. FIG. 4 shows that significant amounts of assembly of all three DNA molecules were evident after 1.5 minutes of chew-back. By 2.5 minutes of chew-back, nearly all of the input DNA is completely assembled.

Example IV

Assembly of the *M. genitalium* Chromosome

The *M. genitalium* chromosome (580,076 bp) is subdivided into 101 cassettes, having an average size of about 6 kb. These ~6 kb cassettes are referred to as cassette 1, cassette 2, and so forth through cassette 101. The cassettes can be prepared using conventional synthetic methods as described, e.g., in Stemmer, et al. (*Gene* (1995) 164:49-53); Young, et al. (*Nucleic Acids Research* (2004) 32:e59); or Smith, et al. (*Proc Natl Acad Sci USA* (2003) 100:15440-15445). Alternatively, they can be purchased from commercial suppliers, such as Blue Heron Biotechnology Inc. (Bothwell, Wash.). The cassettes are joined together sequentially, in the correct order and orientation found in the genome, using a method of the invention.

In a first stage of assembly, the cassettes are joined together four at a time (cassettes 1-4; cassettes 5-8; and so forth through cassettes 78-81, cassettes 82-85, and up to cassettes 98-101), to form 25 larger sets, having an average size of about 24 kb.

In a second stage of assembly, the 25 larger sets are joined together three at a time, to form 8 still larger sets, having an average size of about 72 kb. These still larger sets contain cassettes 1-12; 13-24; up to 78-85 and 86-101).

In a third stage of assembly, the 8 still larger sets are joined together two at a time, to form 4 penultimate sets, having an average size of about 145 kb. These penultimate sets contain cassettes 1-24; 25-48; 49-72 and 73-101.

In a final stage of assembly, the 4 penultimate sets are joined, two at a time, to form two final sets, having an average size of about 290 kb. One of these final sets contains cassettes 1-48, and the other contains original cassettes 49-101.

The two final sets are joined to form the complete *M. genitalium* chromosome.

Example V

Assembly of Four or Eight DNA Molecules, Each DNA having a Length of About 6 kb, and Cloning into a PCR-amplified BAC (Bacterial Artificial Chromosome)

Figure 5:
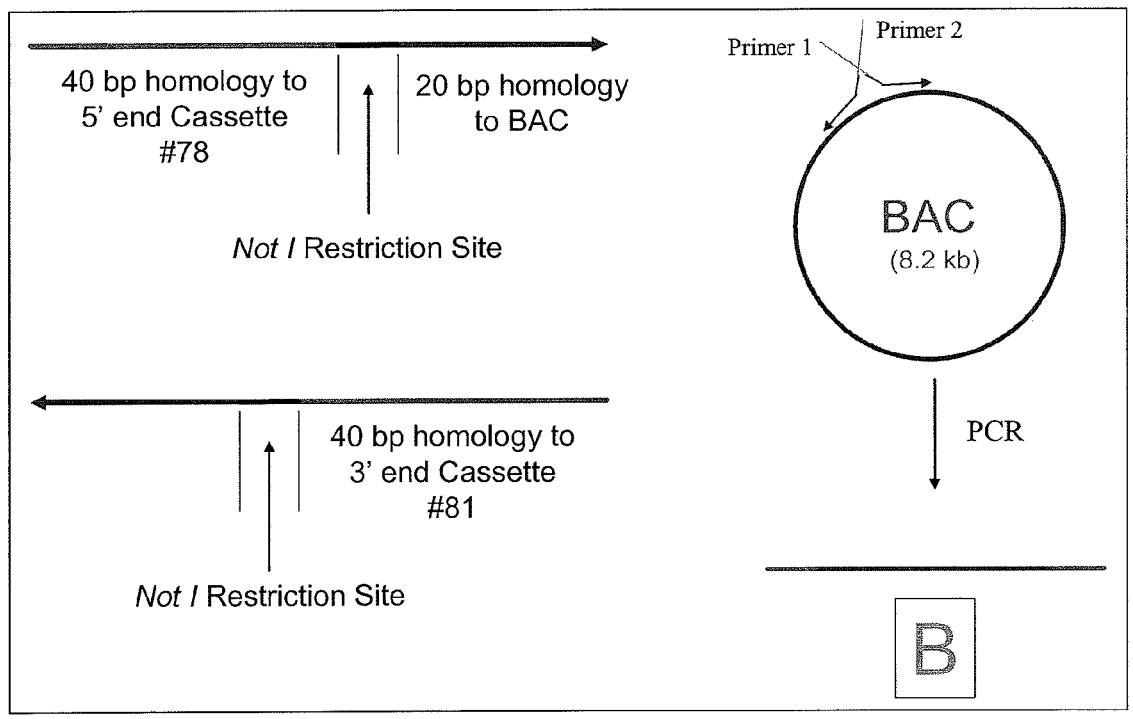
FIG. 5 shows schematically how to prepare a BAC, using PCR, for the insertion of assembled cassettes.

In one experiment, using a method of the invention, four adjacent molecules from the *M. genitalium* chromosome (cassettes #78, 79, 80 and 81), each having about 6 kb, were joined to one another, in the presence of a PCR amplified BAC, to form a molecule of about 24 kb. The 24 kb DNA was simultaneously assembled directly into a BAC, as shown schematically in FIG. 5, such that a unique Not I restriction site was present, and was transformed into *E. coli* (XF *E. coli*). Minipreps were prepared from 10 clones; the assembled, inserted DNA was excised from the BAC with Not I; and the digest was subjected to electrophoresis on a gel. All ten of the transformants contained the desired 24 kb DNA insert. One of the ten was sequenced and was found to be 100% correct. The repair step was shown to be essential to generate the desired molecules. (If desired, the inserts, which are blunt ended, can be cloned into a BAC (or any other vector) without using the procedure illustrated in FIG. 5.)

In a second experiment, cassettes #78, 79, 80 and 81, as well as cassettes #82, 83, 84 and 85, were joined together simultaneously with a PCR amplified BAC as above. Three of the six minipreps tested contained the desired –48 kb insert.

The BAC vector in this example is illustrative. Any suitable vector can be used.

Example VI

Figure 6:
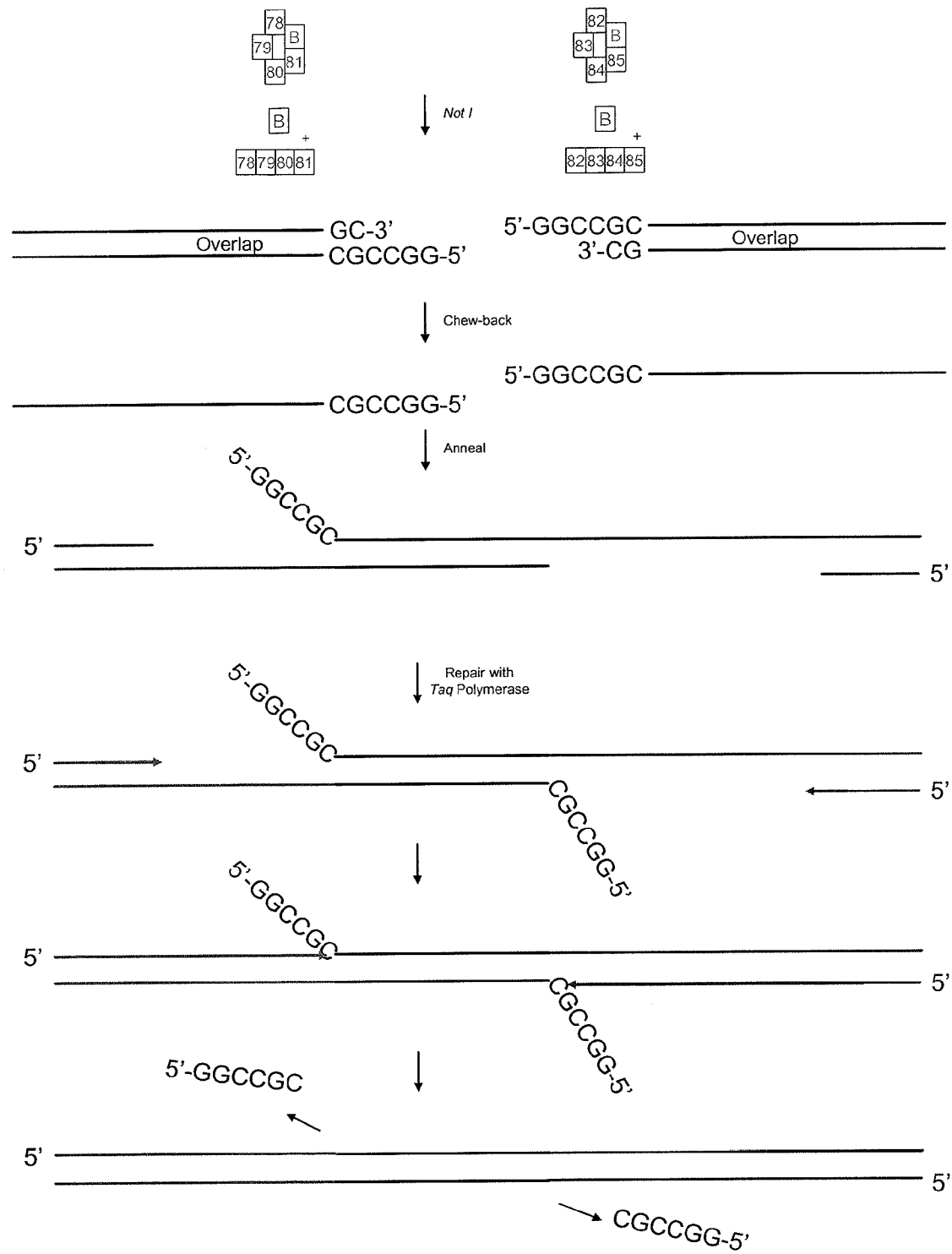
FIG. 6 shows schematically a "second stage" assembly procedure, in which two DNA assemblies, each containing a joined set of 4 cassettes of about 5-6 kb each, are joined together. The cartoon shows that when two overlapping DNA molecules which contain Not I sites are joined by a method of the invention, the Not I sites are removed.

Second Stage Assembly of Four DNA Molecules, Each DNA having a Length of about 6 kb, to Eight DNA Molecules Four adjacent molecules from the *M. genitalium* chromosome (cassettes #78, 79, 80 and 81), each having about 6 kb, were joined simultaneously with a PCR-amplified BAC (about 8 kb) to form a molecule of about 32 kb, as described in Example IV. In parallel, the next four adjacent cassettes (#82, 83, 84 and 85) were joined and assembled into a BAC, by a comparable method. The two assemblies were then excised from their respective BAC vectors with Not I and joined to one another by a method of the invention, to generate a molecule of about 48 kb. FIG. 6 shows schematically that, following the chew-back, anneal, and repair processes, the two molecules were joined correctly, and the Not I site was eliminated.

FIG. 6 illustrates how Not I sequences are removed during this method. Cassettes 78-81 and 82-85 are released from the BAC (B) with Not I. Following cleanup (PCI, ethanol precipitation) of the reactions, 78-81 and 82-85 are assembled, via the about 300 by region of shared homology. Following annealing of these 2 molecules, a portion of the Not I sequence, GGCCGC, still remains. However, since it has no homology, it does not anneal. As Taq polymerase fills in the gaps, it encounters this non-complementary sequence and uses its 5'-3' exonuclease activity (nick translation activity) to remove this sequence. Therefore, no extra sequence is incorporated into the final assembled product. To confirm that the reaction worked as indicated in the figure, cassettes 78-81 and 82-85 were released from their respective BACs, simultaneously assembled into another BAC, cloned, and sequenced. DNA sequencing revealed that there is no extra sequence (e.g., GGCCGC) in the assembled product (i.e., 78-85).

Other restriction enzymes with rare cutting sites, or other restriction sites that are not present in the cassettes to be assembled, can be used in place of Not I, if desired.

Example VII

Conditions for Joining Overlapping DNA Molecules, Using T4 DNA Polymerase in Both the Chew-back and Repair Steps (a) Chew-back:

Overlapping DNAs to be joined are incubated in about equimolar amounts with T4 polymerase in the absence of added dNTPs, under conditions effective to expose the single-stranded overlaps. The optimal time and temperature of incubation depend on, e.g., the size of the overlap, the pH of the reaction mixture, and whether or not PEG is present. The digestion can be carried out at a range of temperatures, from about 23° C. to about 40° C., with a preferred temperature of about 37° C. Typically, a 5 minute reaction at about 37° C. is sufficient for overlaps of about 40-80 bp, and about 15 minutes is sufficient for overlaps greater than 300 bp, when the pH is about 7.5 and about 5% PEG is present.

(b) Annealing:

Generally, in this step, the temperature is raised to about 75° C. for about 20 minutes to heat inactivate T4 DNA polymerase. The single-stranded overhangs of the DNAs are then annealed by slow-cooling, at about 6° C./minute to about 22° C.-24° C. (room temperature).

(i) Temperature for Heat Inactivating the T4 DNA Polymerase

If a heat inactivation step is carried out, the reaction mixture may be incubated at about 75° C. for about 20 minutes. Suitable conditions for heat inactivation are incubation for 20 minutes at about 60 to about 84° C.; preferably, the temperature is about 74° C. to about 78° C.

In other embodiments, the heat inactivation step is not required, provided that: a) following annealing, the reaction is kept at 4° C. (even 23° C. or less can be used for several hours) or b) dNTPs are added immediately. The latter procedure inhibits the 3'-5'exonuclease activity of T4 DNA polymerase.

(ii) Conditions for Annealing the Single-strand DNA Overlaps

Optimal hybridization conditions for sequences of interest (buffers, temperature, and the like) can be designed by conventional procedures. The optimal annealing temperature depends on the melting temperature of the overlap in question. If more than two DNA molecules are to be joined, an investigator should take into account the likelihood of there being multiple temperatures of annealing. To simplify this step, rather than calculating the Tm's for each overlapping sequence, it is preferable, and simpler, to start at the most stringent Tm expected (generally about 75° C.) and to slow cool to about 22° C. This will cover all possible Tm's of a wide variety of possible overlaps. If desired, one can slow cool only to the Tm of the smallest value, rather than cooling down to 22° C. For example, if the smallest Tm is 50° C., it is only be necessary to slow cool to 50° C. Furthermore, if desired, one can slow cool to 4° C. Although this does not provide better annealing, it allows the reaction to be kept cold until the repair mix can be added.

(c) The Filling in (Polymerase)/Ligation Step ("Repair Step")

In this step, T4 DNA polymerase is added back to the reaction along with T4 DNA ligase, dNTPs and ATP. Generally, the reaction is carried out at about 16° C. to about 37° C., for about 30 minutes at 37° C. to about 2 hours at about 16° C. Incubation at 37° C. is preferred, to ensure that the reaction goes to completion. (In other embodiments, Taq DNA polymerase or *E. coli* DNA polymerase I, which have nick-translation activities, are used instead of T4 DNA polymerase for the repair step; these two enzymes create 5'-ends that are phosphorylated and able to be ligated.) The repair reaction works well with a wide range of T4 DNA polymerase (e.g., from about 30 units/ml to about 130 units/ml.)

Depending on the nature of the DNA molecules to be subjected to the DNA polymerase/ligase step, different enzymatic conditions can be employed. For example, if the ends of the DNAs are not phosphorylated (e.g., in reactions in which overlapping ends of 40 by are added by PCR amplification), the gaps can be repaired with Taq DNA polymerase and Taq DNA ligase ("Taq system"). In other embodiments, in which the ends of the DNA are phosphorylated (e.g., in reactions in which the DNA molecules are digested by restriction enzymes to generate 200-400 by overlaps), the repair can be performed with T4 DNA polymerase and T4 DNA ligase ("T4 system").

For the embodiment with 40 by overlaps (Taq system), temperatures between about 37° C. and about 75° C. can be used; temperatures from about 45° C. to about 55° C. are preferred.

For the embodiment with 200 by overlaps (T4 system), temperatures from about 16° C. to about 37° C. can be used; a temperature of about 37° C. is preferred.

For either the 200 by overlaps (T4 system) or for 40 by overlaps (Taq system), incubation times from about 5 minutes to about 18 hours can be used. In general, the repair is achieved by about 5 minutes at 37° C. or 45° C., regardless of the conditions used. Therefore, an incubation time of about 15 to about 30 minutes is generally sufficient.

In a preferred embodiment, buffers, salts, etc., are essentially the same for all of the steps in the method (except, of course, for the addition in some embodiments of dNTPs and repair enzymes following the annealing step).

Example VIII

Conditions for Joining Overlapping 5 DNA Molecules (4 Cassettes and a Vector, pCC1BAC), Using T4 DNA Polymerase for the Chew-back Reaction, and Taq DNA Polymerase and Taq DNA Ligase for the Repair Steps, All Steps in the Presence of 5% PEG Chew-back and Anneal
1. Set up a reaction consisting of the following on ice in a 0.2 ml PCR tube[a]:
   10-1000 ng each substrate DNA to be assembled[b,c]
   20λ 4×CBA Buffer[d]
   0.8λ 10 mg/ml BSA
   1.6λ T4 DNA polymerase (3 U/λ, NEB)
   Add Water to 80λ
   Notes:
   a. This gives a final concentration of 6.25 ng/λ total DNA, 100 µg/ml BSA, 5% PEG-8000, 200 mM Tris-Cl pH 7.5, 10 mM MgCl$_2$, 1 mM DTT, and 0.06 U/λ, T4 DNA polymerase.
   b. 100 ng substrate DNA is ideal for fragments between 5 kb and 8 kb in length. For larger assemblies, increase the amount of DNA (e.g., for fragments 20 kb to 32 kb in length, use 400 ng each substrate).
   c. Avoid having the substrate DNA make up more than half the volume of the reaction. This may inhibit the reaction.
   d. 4×CBA (Chew-back and Anneal) Buffer is 20% PEG-8000, 800 mM Tris-Cl, 40 mM MgCl2, and 4 mM DTT (pH 7.5).
   e. The reaction can be scaled down (e.g., to about 20λ) such that, upon dilution with the repair buffer (see below), the reaction volume doesn't exceed the volume capacity of the tube, or the thermal cycler, thus allowing all reactions to be carried out in a single tube.
2. Add the reaction to a thermal-cycler using the following conditions:
   37° C. 5 minutes*
   75° C. 20 minutes
   0.1° C./s to 60° C.
   60° C. 30 minutes
   0.1° C./s to 4° C.
   4° C. HOLD
   * 5 minutes is sufficient for overlapping DNA segments ≦80 bp. For larger overlaps, extend the time at 37° C. (e.g., 15 minutes for 300 bp overlaps).
3. If desired, the assembly reaction can be analyzed by conventional methods of gel electrophoresis.

Repair (Perform at 4° C. (e.g., on Ice))
4. Remove 102, and add 25.75λ TRB (Taq Repair Buffer), which consists of the following:
   20.26λ water
   3.75λ 40% PEG-8000
   0.8λ 10 mM dNTPs (each dNTP is 10 mM)
   0.4λ 100 mM NAD
   0.15λ 2M MgCl$_2$
   0.39λ 1M DTT
5. Mix well then add 4.0λ Taq DNA Ligase (40 U/λ, NEB)
6. Mix well then add 0.25λ Taq DNA Polymerase (5 U/λ, NEB)
Note: This gives a final concentration of 1.5 ng/λ total DNA, 25 µg/ml BSA, 5% PEG-8000, 50 mM Tris-Cl pH 7.5, 10 mM MgCl$_2$, 10 mM DTT, 200 µM each dNTP, 1 mM NAD, 4 U/λ Taq DNA Ligase, and 0.03 U/λ Taq DNA Polymerase.
7. Incubate at 45° C. for 15 minutes.

Transformation
8. Transform 2λ of the assembly reaction into 20λ TransforMax™ EPI300™ (Epicentre) electrocompetent *E. coli* using the following parameters:

| | |
|---|---|
| Voltage (V) | 1200 |
| Capacitance (µF) | 25 |
| Resistance (Ω) | 200 |
| Cuvette (mm) | 1 |

9. Recover cells in 500 µl SOC medium, 2 hours at 37° C.
10. Plate 100 µl onto LB Agar+12.5 µg/ml chloramphenicol.
11. Incubate at 37° C. for 18-24 hours[a].
Notes:
a. For the assembly of 5 overlapping DNA segments (including the vector), expect 200-300 transformants. In general, 100% of the transformants tested are correct.

Example IX

Exemplary Applications of this Technique

1. T4 DNA Polymerase
   a. Chew-back at 37° C.
   b. Anneal by slow cooling 75° C. to 22° C.
   c. Add dNTPs, T4 DNA polymerase, and T4 DNA ligase to repair
2. T4 DNA Polymerase+*E. coli* RecA
   a. Chew-back/Anneal at 37° C. in presence of *E. coli* RecA
   b. Add dNTPs and T4 DNA ligase to repair
3. Vent DNA Polymerase[A]
   a. Chew-back at 65° C.
   b. Cleanup reaction by PCI Extraction/ethanol ppt.
   c. Anneal by slow cooling 75° C. to 22° C.[B]
   d. Add dNTPs, Taq DNA polymerase, and Taq DNA ligase to repair[C]
4. Vent DNA Polymerase+*E. coli* RecA[D]
   a. Chew-back at 65° C. in presence of *E. coli* RecA
   b. Anneal at 37° C.
   c. Add dNTPs, Taq DNA polymerase, and Taq DNA ligase to repair
5. One Step Exonuclease III
   a. In a thermal cycler, setup a mix consisting of DNA substrates, exonuclease III, RecA, Taq DNA polymerase, Taq DNA ligase, dNTPs, and buffer supporting activity of all enzymes.
   b. Chew-back/Anneal at 37° C.
   c. Raise temperature to 55° C. for repair (At 55° C., ExoIII is inactive)

Notes:

A. Any enzyme having 3'-5' exonuclease activity can be used in this system. Examples include Exonuclease III, Phi29 DNA Polymerase—dNTPs, T7 DNA Polymerase—dNTPs, DNA Polymerase I—dNTPs, Klenow DNA Polymerase—dNTPs, Deep Vent DNA Polymerase—dNTPs, 9° N$_m$ DNA Polymerase—dNTPs and Phusion™ High Fidelity DNA Polymerase—dNTPs.

B. Maximum annealing may be occurring in the cleanup process (PCI, ethanol ppt, speed vac to dry pellets).

C. The Taq repair system is preferred. Like T4 DNA Polymerase, Taq DNA polymerase doesn't have strand displacement activity. However, Taq DNA polymerase has nick translating activity, which T4 DNA polymerase does not have. The nick translating activity ensures that the 5' phosphate of substrate 1 is adjacent to the 3' hydroxyl of substrate 2 and therefore, in position to be ligated. Furthermore, since Taq polymerase has nick translating activity, it is not necessary to phosphorylate the DNA substrates.

D. It may be better to use Phusion DNA Polymerase in place of Vent DNA polymerase. Phusion™ DNA Polymerase has a strong 3'-5' exonuclease activity and no strand displacement activity. Therefore, Phusion™ DNA Polymerase is good for both the chew-back and repair reactions. However, since Phusion™ Polymerase doesn't have nick translation activity, the substrates would need to be phosphorylated. If Vent DNA Polymerase is used in the chew-back reaction, a different polymerase (e.g., Taq DNA polymerase) would need to be used for the repair reaction, since Vent has strand displacement activity.

Example X

Recombination of DNA Molecules in an Isothermic Manner (by Using a Protein such as RecA Instead of a Heating/Cooling Step to Anneal the Single-stranded Overhangs)

Figure 7:
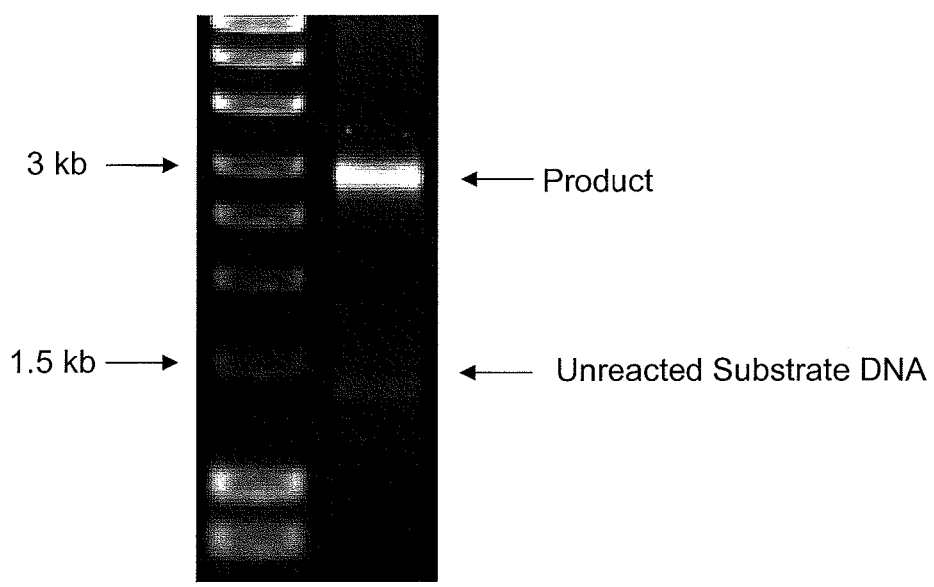
FIG. 7 shows in vitro recombination of two DNA molecules, in which *E. coli* RecA protein is used to enhance the annealing of single-stranded overhangs instead of a heating/cooling reaction.

Two DNA were recombined in vitro, using *E. coli* RecA to enhance the annealing of single-stranded overhangs. In this illustrative Example, the two DNA fragments used were amplified by PCR from a shuttle vector (pRS415); the fragments were designed to have the approximate sizes of 1.6 kb and 1.4 kb, and to contain a 40 bp overlap. T4 DNA polymerase was used for the chew-back reaction (in the absence of dNTPs) and for the fill-in reaction (in the presence of added dNTPs). Approximately 1.6 mg RecA, 100 ng substrate DNA, and 0.6 units T4 DNA polymerase were added to a reaction 10 µl reaction with a final concentration of 1× T4 DNA ligase buffer (NEB). The reaction took place at 37° C. for 30 minutes. After 30 minutes, a 10 µl repair mix was added which consisted of 400 µM dNTPs, and 400 units of T4 DNA ligase in 1× T4 DNA ligase buffer. The reaction was allowed to continue at 37° C. for an additional 15 minutes. Following a PCI extraction, the in vitro recombination was assessed on a 1% agarose gel. FIG. 7 shows that the fragments were efficiently recombined.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding specific embodiments are to be construed as merely illustrative, and not limiting of the scope of the invention in any way whatsoever. The entire disclosure of all applications (including U.S. provisional applications Ser. No. 60/707,177, filed Aug. 11, 2005 and 60/800,400, filed May 16, 2006), patents, publications (including reference manuals) cited above and in the figures, are hereby incorporated in their entirety by reference.

The invention claimed is:

1. An in vitro method for joining a first set of double-stranded (ds) DNA molecules, comprising:
   (a) providing two or more dsDNA molecules to be joined in a reaction mixture, wherein, for each pair of dsDNA molecules to be joined, a distal region of a first DNA molecule and a proximal region of a second DNA molecule share a region of overlapping sequence homology;
   (b) treating the provided dsDNA molecules with a substantially purified enzyme having 5'-3' exonuclease activity, whereby a single-stranded overhanging portion is generated in each of the dsDNA molecules by 5'-3' exonuclease digestion, wherein each overhanging portion contains the region of homology or a portion thereof sufficient to specifically anneal to the overhanging portion in the other molecule of the pair;
   (c) incubating the DNA molecules generated in step (b), under conditions whereby they anneal through the regions of homology or portions thereof; and
   (d) treating the annealed molecules with a substantially purified polymerase and a substantially purified compatible ligase, under conditions whereby remaining single-stranded gap(s) are filled in by the polymerase and nicks are sealed by the ligase; thereby joining the dsDNA molecules;

wherein a crowding agent is present in the reaction mixture during each of steps (b), (c), and (d); and wherein the overhanging portions are created without the use of restriction enzymes.

2. The method of claim 1, wherein the crowding agent is a polymer selected from the group consisting of PEG, Ficoll, and dextran.

3. The method of claim 2, wherein the concentration of PEG in the reaction mixture is about 5% PEG.

4. The method of claim 1, wherein the polymerase in step (d) is Taq DNA polymerase, T4 DNA polymerase, T7 DNA polymerase, DNA polymerase I, Klenow DNA polymerase, Pfu polymerase, or Phusion™ High-Fidelity polymerase.

5. The method of claim 1, wherein the compatible ligase in step (d) is Taq ligase.

6. The method of claim 1, wherein the enzyme having 5'-3' exonuclease activity is phage T7 exonuclease (phage T7 gene 6 product), phage lambda exonuclease, Redα, of lambda phage, or RecE ofRac prophage.

7. The method of claim 1, wherein the incubating in step (c) is carried out by subjecting the molecules to conditions effective to separate any single-stranded portions that have annealed and, optionally, to inactivate the enzyme having 5'-3' exonuclease activity, followed by slowly cooling the molecules to about 24° C. or less, under conditions effective to allow the single-stranded overhanging portions to anneal.

8. The method of claim 7, wherein subjecting the molecules to conditions effective to separate any annealed portions and, optionally, to inactivate the enzyme having 5'-3' exonuclease activity, includes heating said molecules to 75° C. plus or minus 5° C.

9. The method of claim 1, wherein the treating in step (d) is performed at between 45° C. and 55° C.

10. The method of claim 1, wherein the incubation in step (c) is carried out in the presence of a protein that enhances the binding of single-stranded overhanging portions containing homologous regions or portions thereof.

11. The method of claim 10, wherein the protein that enhances the binding of the single-stranded overhanging portions is recA, E. coli single-stranded binding protein (SSB), T7 SSB (T7 gene 2.5 product), or T4 gene 32 protein.

12. The method of claim 1, wherein at least four dsDNA molecules are joined and each shared region of sequence homology is unique for each pair of DNA molecules joined.

13. The method of claim 12, wherein at least eight dsDNA molecules are joined.

14. The method of claim 1, wherein the DNA molecules to be joined are at least 5 kb in length.

15. The method of claim 1, wherein, for at least one pair of dsDNA molecules to be joined, the region of sequence homology comprises at least 20 non-palindromic nucleotides in length.

16. The method of claim 1, wherein, for at least one pair of dsDNA molecules to be joined, the region of sequence homology comprises at least 300 nucleotides in length.

17. The method of claim 1, wherein steps (b) through (d) are carried out in a single reaction vessel.

18. The method of claim 1, further comprising:
(i) joining a second set of dsDNA molecules by performing steps (a) through (d); and
(ii) performing a second stage assembly, comprising steps (a) through (d), wherein the dsDNA molecules provided in step (a) comprise a product produced by joining the first set and a product produced by joining the second set.

19. The method of claim 1, wherein the method is automated and highthroughput.

20. The method of claim 1, wherein a PCI clean-up procedure is not carried out following the exonuclease digestion.

21. The method of claim 1, wherein the overhanging portions are generated without the use of a restriction enzyme.

22. The method of claim 1, wherein the dsDNA molecules are joined in a predefined order and orientation.

23. The method of claim 1, wherein steps (b) and (c) are performed in the same reaction mixture, containing the same buffer and reaction components.

24. The method of claim 1, wherein steps (b) and (c) are performed in the same reaction vessel and the vessel is not opened between steps (b) and (c).

25. The method of claim 2, wherein the size of the PEG is within the range of PEG 4,000 to PEG 20,000.

26. The method of claim 2, wherein the size of the PEG is PEG 8000.

* * * * *